(12) United States Patent
Sato et al.

(10) Patent No.: US 6,760,101 B2
(45) Date of Patent: Jul. 6, 2004

(54) METHOD FOR INSPECTING EXPOSURE APPARATUS

(75) Inventors: Kazuya Sato, Tokyo (JP); Soichi Inoue, Yokohama (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 454 days.

(21) Appl. No.: 09/783,295

(22) Filed: Feb. 15, 2001

(65) Prior Publication Data

US 2001/0019407 A1 Sep. 6, 2001

(30) Foreign Application Priority Data

Feb. 15, 2000 (JP) ........................................ 2000-036690

(51) Int. Cl.$^7$ .............................................. G01N 21/00
(52) U.S. Cl. .................................................. 356/237.4
(58) Field of Search ........................... 356/237.1–237.6, 356/122–124; 355/53–77; 430/5, 269, 322–324

(56) References Cited

U.S. PATENT DOCUMENTS

| | | | |
|---|---|---|---|
| 4,906,081 A | * 3/1990 | Yasuda | ........................ 359/723 |
| 5,493,402 A | * 2/1996 | Hirukawa | .................... 356/400 |
| 5,973,771 A | * 10/1999 | Hibbs et al. | ................. 356/121 |
| 6,317,198 B1 | 11/2001 | Sato et al. | |

FOREIGN PATENT DOCUMENTS

JP    2000-21732    1/2000

OTHER PUBLICATIONS

Sato, K. et al., "Method of Examining an Exposure Tool", Ser. No. 09/345,758, filed on Jul. 1, 1999.

* cited by examiner

Primary Examiner—Tu T. Nguyen
(74) Attorney, Agent, or Firm—Finnegan, Henderson, Farabow, Garrett and Dunner, L.L.P.

(57) ABSTRACT

Light emitted from an illumination optical system is guided to a photomask where a pattern is formed of an optical member including a light transmission pattern as a diffraction grating pattern, in which a light transmission part and a opaque part are repeated in a finite period and a periphery of the light transmission pattern is shielded by a opaque area, such that a plurality of ratios are given between the light transmission part and the opaque part. Diffraction light, which has passed through the photomask, is irradiated on a projection optical system, thereby to transfer a pattern reflecting an intensity distribution of the diffraction light to a wafer. A change of transmittance depending on a light path of the projection optical system is measured, based on a pattern image of the diffraction light transferred to the wafer. Pattern transfer is carried out in a non-conjugate state.

15 Claims, 15 Drawing Sheets

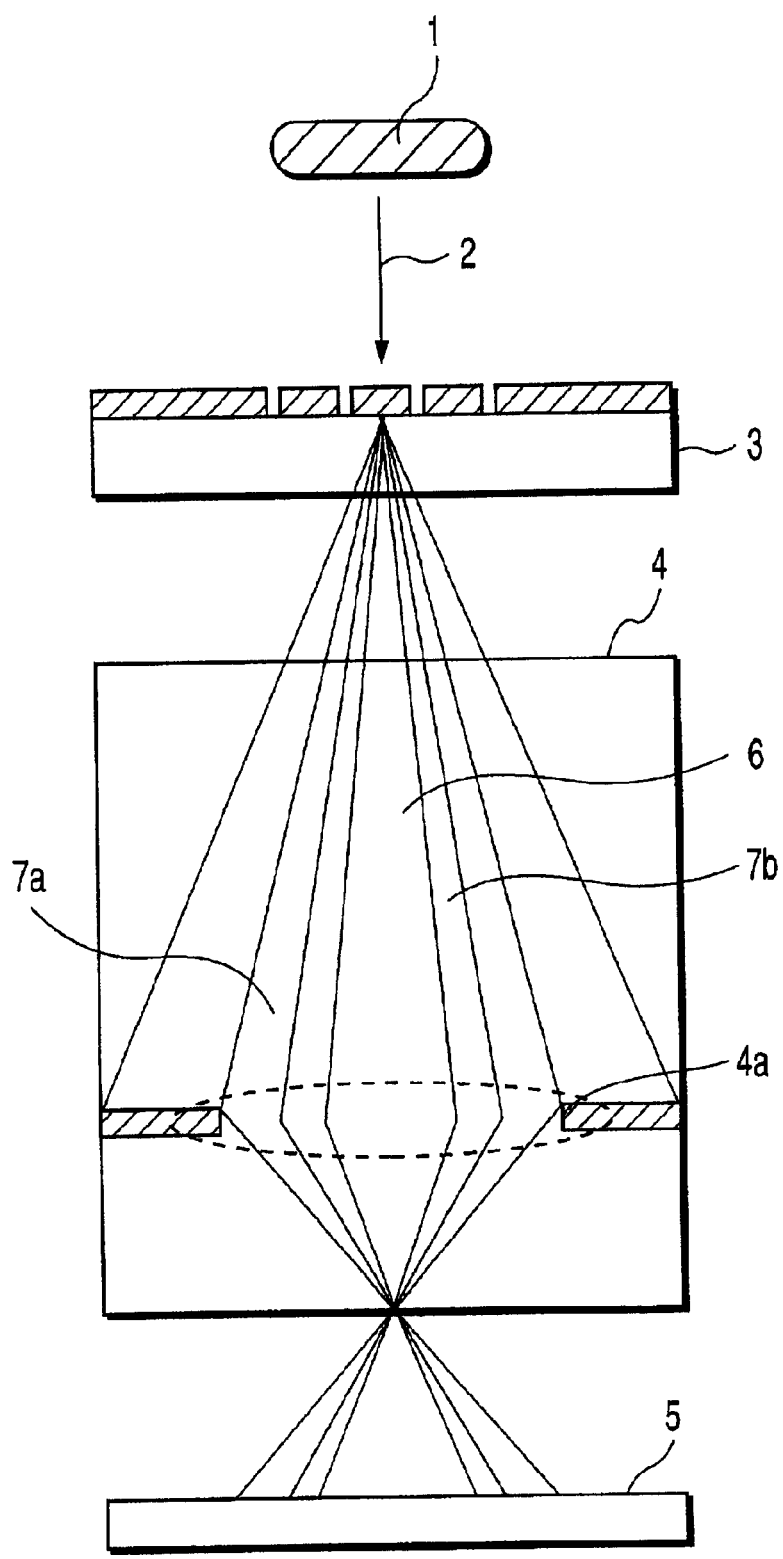
F I G. 2

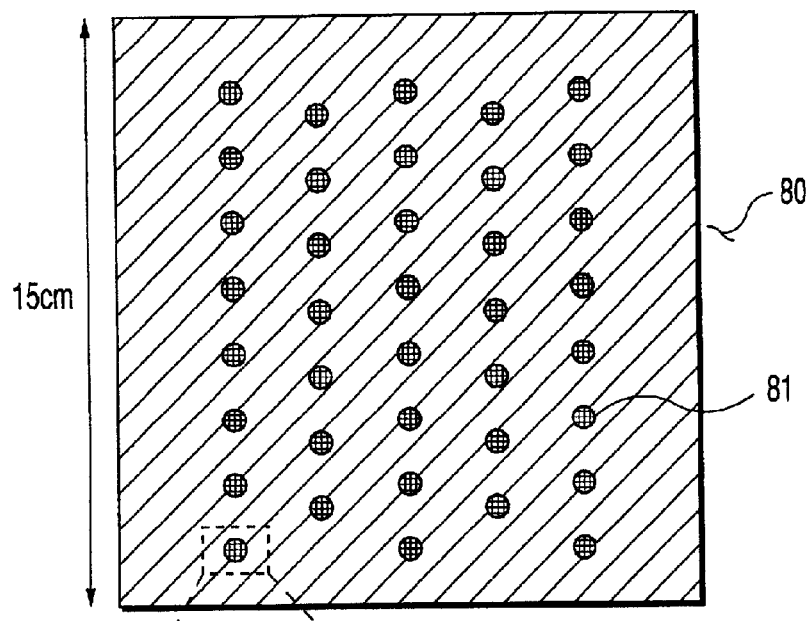
FIG. 9A
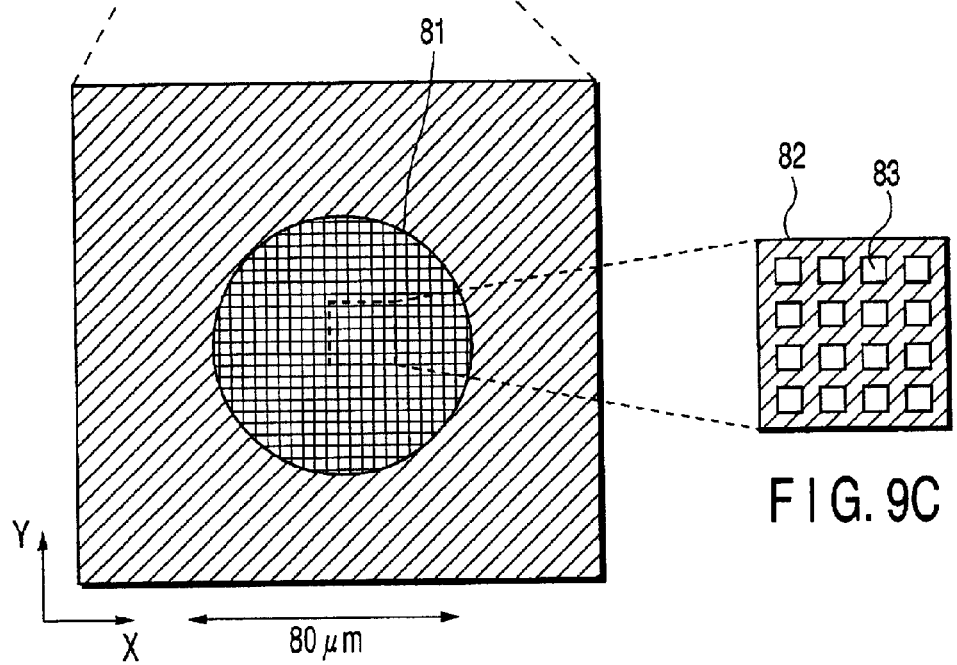
FIG. 9B
FIG. 9C

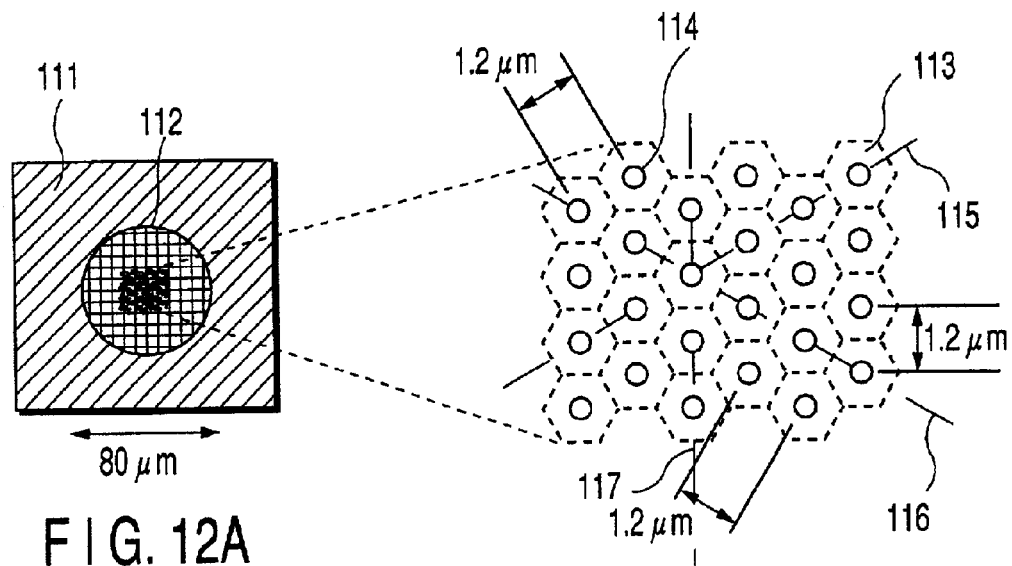
F I G. 12A  F I G. 12B
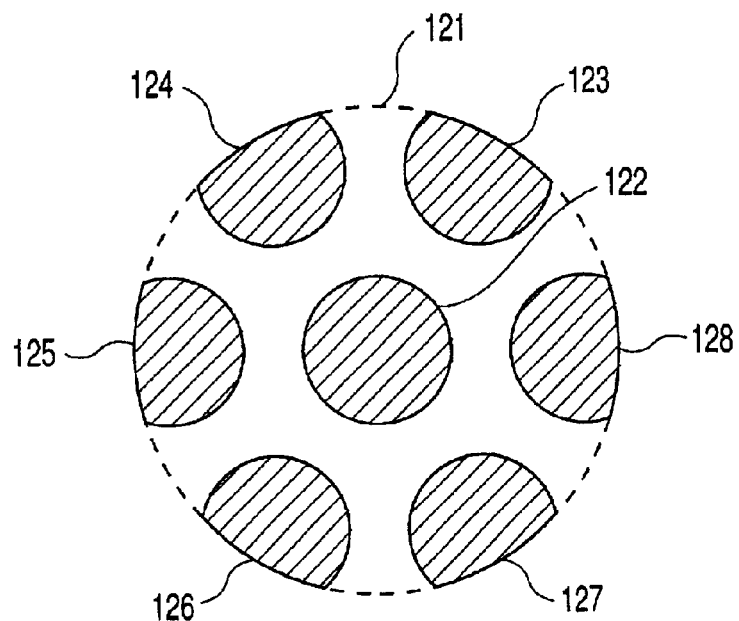
F I G. 13

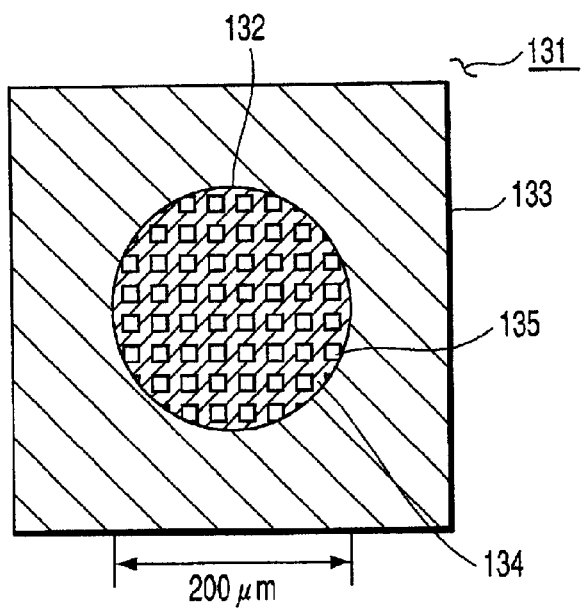
F I G. 14
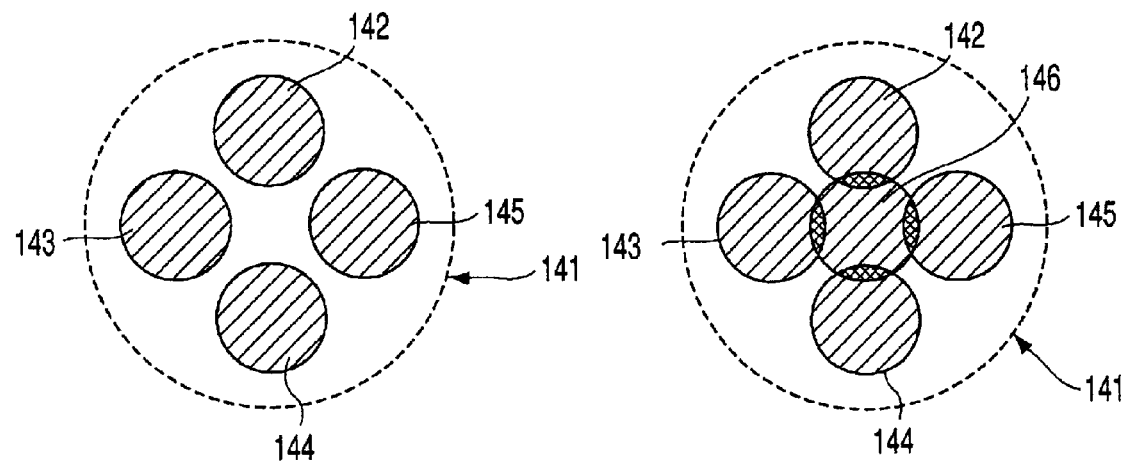
F I G. 15A    F I G. 15B

METHOD FOR INSPECTING EXPOSURE APPARATUS

CROSS-REFERENCE TO RELATED APPLICATIONS

This application is based upon and claims the benefit of priority from the prior Japanese Patent Application No. 2000-036690, filed Feb. 15, 2000, the entire contents of which are incorporated herein by reference.

BACKGROUND OF THE INVENTION

1. Field of the Invention

The present invention relates to a method for inspecting a projection exposure apparatus used for manufacturing a semiconductor device, and particularly to a method for inspecting performance of a projection optical system of an exposure apparatus.

2. Description of the Related Art

A lithography technique is generally used to manufacture a circuit pattern of a semiconductor device. In a projection exposure apparatus used in a lithography process, light emitted from an illumination optical system enters a photomask on which a circuit pattern is drawn. Light passing through the photomask is converged by a projection optical system. Further, in general cases, the circuit pattern of the photomask is focused and projected on a substrate applied with a photosensitive material, e.g., a silicon wafer applied with photoresist.

Recently, as the semiconductor device pattern to be formed is downsized, the dimension of the pattern to be formed by the optical lithography becomes severer.

In case of the exposure apparatus, as the pattern of the semiconductor device in comparison with the exposure wavelength is shrunk more, diffraction of light becomes more remarkable. Also, it is known that the diffraction angle increases as the period of the pattern decreases. To form a micro pattern, the diffraction light propagating in the direction in which it goes away from the optical axis needs to be captured and converged onto the wafer. Therefore, the diameter of the projection optical system needs to be increased in order to form a more microscopic pattern. In other words, the numerical aperture NA of a projection optical system needs to be increased. In case of the exposure using a photomask which has a one-dimensional periodic pattern such as line & space pattern, a plurality of discrete diffraction light are occurred. The discrete diffraction light are straight zeroth-order diffraction light, first-order up to higher-order diffraction light which have predetermined diffraction angle. In order to form a one-dimensional periodic pattern on the wafer, first-order diffraction light needs to be captured and converged with zeroth-order diffraction light.

Meanwhile, if the projection lens forming part of the projection optical system becomes large, a problem occurs in that light transmittance depending on the light path changes. In case of exposing a relatively large pattern with respect to the exposure wavelength, the light diffraction angle is small. In this case, only the portion of light that passes through the optical axis of the projection lens contributes to focusing of an image. That is, the paths of zeroth-order diffraction light and first-order diffraction light that are used for focusing an image are different from each other. Accordingly, the intensity of each diffraction light is not influenced by changes of the transmittance of the projection optical system.

In contrast, the diffraction angle is large in case of exposing a micro pattern, and therefore, zeroth-order diffraction light and first-order diffraction light are different from each other. Accordingly, if the transmittance in the projection optical system changes depending on light paths, diffraction light which reaches a wafer is influenced by changes of the transmittance, and as a result, the intensity of each diffraction light changes.

In conjunction of design of the projection optical system, changes of the transmittance depending on the light paths are not caused. But in practice, the drawbacks can be occurred imperfect anti-reflection coating on lens surface, light absorption of lens material, and the like. However, proposals have not yet been made for a method of directly measuring this phenomenon without disassembling the exposure apparatus.

A transmittance change depending on the light paths causes the intensities of zeroth-order diffraction light and first-order diffraction light to change. Since photoresist pattern on a wafer is formed by interference between these diffraction lights, a change of the intensities influences the pattern image focusing performance. As a result of this, it is considered that the micro pattern transferring performance of the projection optical system is deteriorated.

If a micro periodic pattern is formed by interference between zeroth-order diffraction light and first-order diffraction light, light generated by the interference constructs a bright part and a dark part. The degree of brightness is expressed as an amount of contrast. If bright and dark parts are clearly distinguished from each other, it is called "high contrast". The higher the contrast of interference light, the easier the transfer of the pattern onto the wafer. In other words, the contrast should desirably be high in order to widen the focus margin and the exposure dose margin. The contrast is determined by amplitude and phases of lights which interference each other.

If a circuit pattern is designed supposing that drawbacks described above do not occur, the contrast of interference light formed on the wafer is rendered insufficiently high. As a result, no pattern may be formed. At present, shrinkage of patterns has progressed and lithography design using simulations has come to have a significant meaning. It is undesirable that unexpected drawbacks of this kind occur in the exposure apparatus. In the process of assembling an exposure apparatus, drawbacks should be removed or extents of drawbacks should previously measured and which then have to be taken into consideration in case of estimate and designing of to-be-formed pattern based on exposure simulations.

An example of measurement of contrast, which has been conventionally carried out, will be explained with reference to FIG. 1. FIG. 1 shows relationship between formed photoresist patterns (left side) and relative light intensities I (=1/D) (right side). The contrast is expressed by the following expression with use of a light intensity I1 at peaks of light intensity and a value I5 at a minimum light intensity between peaks.

$$(\text{contrast}) = (I1 - I5)/(I1 + I5)$$
$$= (1/D1 - 1/D5)/(1/D1 + 1/D5)$$
$$= (D5 - D1)/(D5 + D1)$$

In the expression, the intensity I5 at which the light intensity comes to peaks is an intensity of the minimum between peaks of light intensities. Although presence or absence of reduction of the contrast can be confirmed by the method shown in FIG. 1, factors which cause reduction of the contrast is very difficult to specify.

Another phenomenon which is caused by a change of the diffraction intensity is a positional shift of pattern depending on focusing onto a wafer, which is caused by the gravity center of the intensity of the diffraction light shifts from the center of the projection optical system. Where a line-and-space pattern are cited as an example, two of positive and negative first-order diffraction lights are generated with a center of zeroth-order diffraction light taken as a symmetry point. If there is a difference between intensities of the positive and negative first-order diffraction lights, the position where the pattern is formed shifts depending on the defocus amount of the wafer.

The shift of the position where the pattern is formed depending on the defocus amount of the wafer is occurred due to factors other than a transmittance change depending on the light paths, such as coma aberration or illumination telecentricity error. Therefore, it is difficult to specify the factor which causes the shift of the position only by the measurement of the relationship between the defocus and misalignment of the pattern.

BRIEF SUMMARY OF THE INVENTION

The present invention has an object of providing a method for inspecting an exposure apparatus capable of specifying a change of the light transmittance depending on the light path.

The present invention provides a method for inspecting an exposure apparatus, comprising: a step of guiding light emitted from an illumination optical system to a photomask where a pattern is formed of an optical member including a light transmission pattern as a diffraction grating pattern, in which a light transmission part and a opaque part are repeated in a predetermined direction, a plurality of ratios are given between a length of the light transmission part and a length of the opaque part in a repetition direction, and a periphery of the light transmission pattern is shielded by a opaque area, such that a plurality of ratios are given between the light transmission part and the opaque part;

a step of irradiating diffraction light, which has passed through the photomask, on a projection optical system, thereby to transfer a pattern reflecting an intensity distribution of the diffraction light to a wafer; and a step of measuring a change of transmittance depending on a light path of the projection optical system, based on a pattern image of the diffraction light transferred to the wafer.

When inspecting a projection optical system of an exposure apparatus in the present invention, light emitted from a light source is guided to a photomask and light passing through the photomask is irradiated on like normal pattern exposure, thereby to transfer a pattern image reflecting an intensity distribution of the diffraction light on a wafer.

When transferring a pattern in the present invention, a light transmission pattern in which light transmission parts and opaque parts are repeated at a finite period is formed on a photomask, and therefore, diffraction light is obtained.

In addition, the photomask and the wafer are rendered non-conjugate with respect to the projection optical system. In this manner, pattern transfer can be performed in a state in which diffraction lights of zeroth-order up to higher-order are separated from each other and diffraction light components have sufficient sizes. In the present invention, where NA is a numerical aperture of the projection optical system in a wafer side, $\lambda$ is a exposure length, $\sigma$ is a coherence factor, and M is a magnification of the photomask, the period of the diffraction grating pattern is set so as to satisfy $p > M\lambda/NA(1+\sigma)$. In this manner, first-order diffraction light can be transferred to the wafer without being shaded by the aperture stop, so that the light intensity distribution can be inspected based on the transferred pattern image.

By observing patterns thus obtained on a wafer, it is possible to measure changes of light transmittance depending on light paths.

Specifically, by taking exposure using light transmission patterns which have the light transmission parts and the opaque parts the ratio of which (the ratio between the light transmission parts and the opaque parts) are different from each other, a plurality of resist patterns are transferred onto the wafer. By analyzing the resist patterns, an equal-intensity contour plot of light intensity distributions is obtained. It is thus possible to measure the light transmittance depending on the paths of the projection optical system based on the contour plot of light intensity distributions.

More desirably, the photomask where the diffraction patterns are formed is constructed as a attenuated phase shift mask. Namely, the diffraction pattern is constructed by a light transmission part and a semi-transparent phase shift part at which the phase is shifted from the light transmission part. In this respect, the duty ratio of the diffraction grating can be adjusted so that the intensity of zeroth-order diffraction light can be approximately zero. In this case, patterns depending on the zeroth-order diffraction light are not transferred. Therefore, only the first-order diffraction light can be observed so that first-order diffraction light components close to the light axis of the optical system of the exposure apparatus can be observed.

In addition, the non-conjugate state in which the photomask and the wafer are non-conjugate with respect to the projection optical system is realized by arranging the opaque part of the light optical member on a surface opposite to a surface where the optical member of the photomask used for device pattern exposure is arranged. That is, the photomask is attached to a mask stage, reversed from the state in case of device pattern exposure. In this manner, a non-conjugate state can be created very simply while maintaining the structure of the exposure apparatus used for pattern exposure. Of course, at least one of the photomask and the wafer may be shifted from a conjugate position in the light axis direction.

Also, conditions are set so as to satisfy a relationship of $0.4(nd\lambda)^{1/2} \leq r \leq (nd\lambda)^{1/2}$ where the light transmission pattern has a circular shape having a radius r, d is thickness of the photomask, $\lambda$ is an exposure wavelength, and n is a refractive index of material of the photomask at the exposure wavelength $\lambda$. In this manner, the resolution of the transferred pattern image can be improved and the resist patterns which are suitable for measurement can be obtained.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a view showing the entire structure of an exposure apparatus as a target according to the first embodiment of the present invention;

FIGS. 9A, 9B, 9C are views showing the entire structure of a photomask used in the second embodiment of the present invention;

FIGS. 12A and 12B are plan views showing main parts of a photomask used in the third embodiment of the present invention;

FIG. 13 is a view schematically showing photoresist patterns obtained by pattern exposure according to the embodiment;

FIG. 14 is a plan view showing a photomask used for inspecting an exposure apparatus according to the third embodiment of the present invention;

FIGS. 15A and 15B are views showing shapes of photoresist patterns formed by an inspection method according to the embodiment, compared with another embodiment;

DETAILED DESCRIPTION OF THE INVENTION

Figure 1:
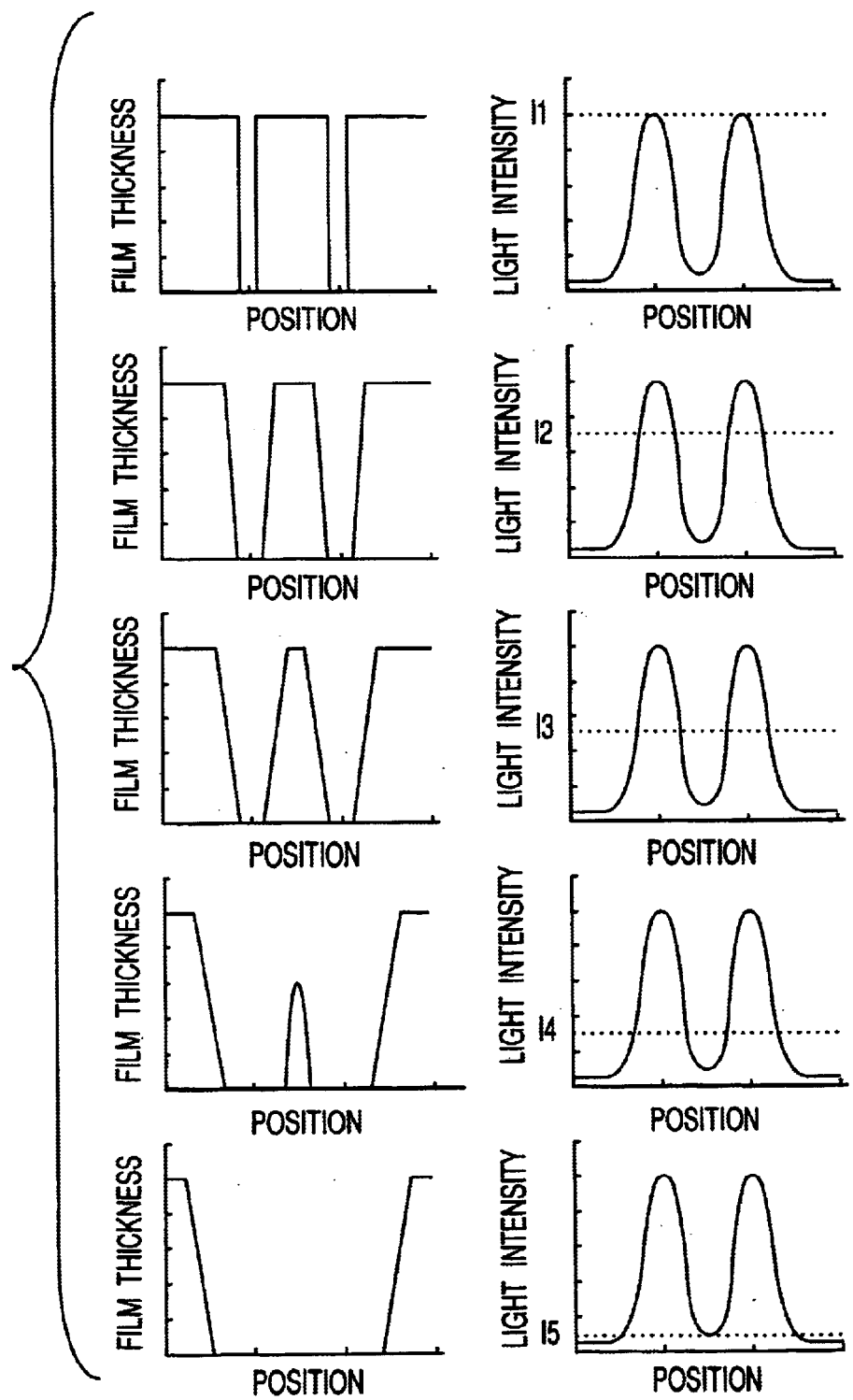
FIG. 1 are an explanatory view for a conventional contrast measurement method.

In the following, embodiments of the present invention will be explained with reference to the drawings.

(First Embodiment)

FIG. 2 is a view showing the entire structure of an exposure apparatus as an inspection target according to the first embodiment of the present invention. In the present embodiment, explanation will be made of a case of an example in which a KrF excimer laser reduction projection exposure apparatus ($\lambda$: 248 nm, NA: 0.6, $\sigma$: 0.3, mask magnification M: 4) is inspected.

FIG. 2 is a view showing the entire structure of a reduction projection exposure apparatus as an inspection target of the present embodiment. As shown in FIG. 2, a light source 1, a photomask 3, a projection optical system 4, and a wafer 5 are arranged in this order along the light path of exposure light 2.

Figure 3A:
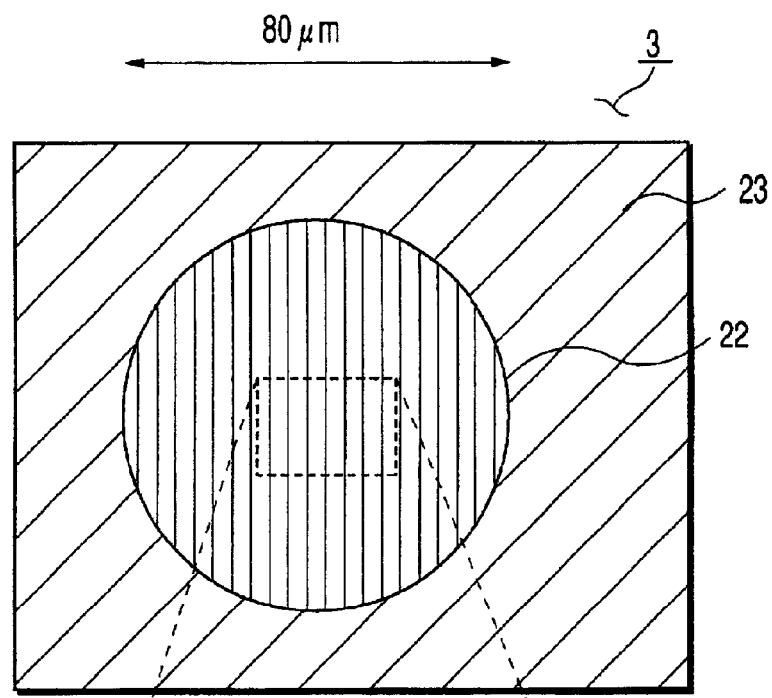
FIGS. 3A and 3B are views showing the entire structure of a photomask 3 incorporated in the exposure apparatus according to the embodiment.
Figure 3B:
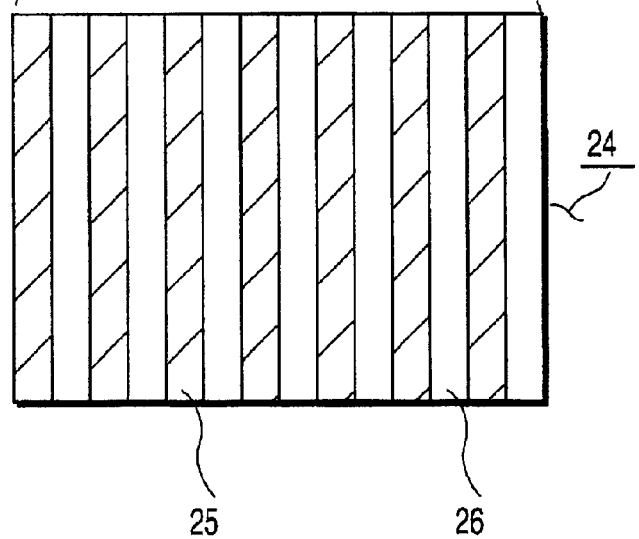

FIGS. 3A and 3B are views showing the photomask 3 incorporated in the exposure apparatus. As shown in the plan view of the entire structure in FIG. 3A, a pinhole pattern 22 is arranged as a light transmission pattern in the photomask 3. Further, the periphery of this pinhole pattern 22 serves as a opaque area 23. The diameter of the pinhole pattern 22 as dimensions on a photomask is 80 $\mu$m.

FIG. 3B is an enlarged view of a part of the pinhole pattern 22 of the photomask 3. As shown in FIG. 3B, a diffraction pattern 24 constructed by line and space patterns is formed on the pinhole pattern 22 of the photomask 3. This diffraction pattern 24 includes opaque parts 25 and light transmission parts 26. The period is 1.6 $\mu$m and the ratio between the width of each shielding part 25 and the width of each light transmission part 26 is 1:1.

In the present embodiment, the period of the diffraction gratings satisfies p>M$\lambda$/NA(1+$\sigma$), where the aperture of the projection optical system 4 in the side of the wafer 5 is NA and the coherence factor of the exposure apparatus is $\sigma$, the exposure wavelength is $\lambda$, and the magnification of the mask is M. As a result of this, zeroth-order diffraction light and first-order diffraction light can be transferred to the wafer 5, separated from each other. Accordingly, the light intensity distribution can be inspected without interference with zeroth-order diffraction light.

The photomask 3 described above is provided such that the surface where the pattern is formed is arranged in the side of the illumination optical system 1 along the light path formed from the illumination optical system to the wafer 5, as shown in FIG. 2, and pattern exposure is carried out. Conventionally, in case of device pattern exposure, the photomask 3 is set such that the actual pattern forming surface is set in the side of the wafer 5 along the light path formed from the illumination optical system to the wafer 5. By attaching the photomask 3 to a mask stage with the mask reversed from the arrangement in actual pattern exposure as in the present embodiment, the wafer 5 and the photomask 3 can be rendered non-conjugate with respect to the projection optical system 4.

Figure 4:
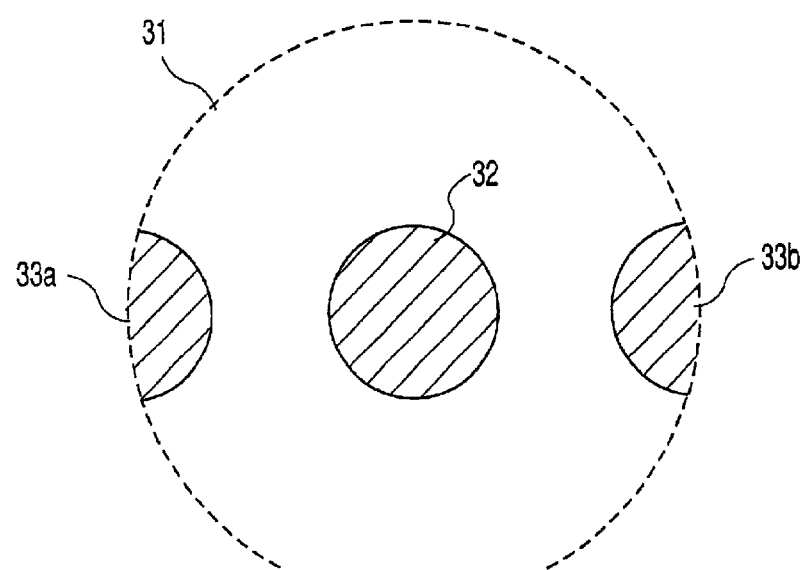
FIG. 4 is a plan view showing photoresist patterns obtained by pattern exposure according to the embodiment.

FIG. 4 is a plan view schematically showing photoresist pattern formed on the wafer 5 by pattern exposure. As shown in FIG. 4, the light reach area 31 is an area to which light can reach from the illumination optical system 1 through the projection optical system 4. This is because the light which passes through the projection optical system 4 by a pupil 4 forming part of the projection optical system 4 is converged, and a boundary line which defines the light reach area 31 corresponds to the outer periphery of the pupil 4a.

As shown in FIG. 2, zeroth-order diffraction light 6, positive first-order diffraction light 7a, and negative first-order diffraction light 7b pass through the inside of the pupil 4a. Accordingly, a zeroth-order diffraction pattern 32 and positive and negative first-order diffraction light patterns 33a and 33b are created on the wafer 5. These diffraction light patterns 32, 33a, and 33b have shapes similar to the cross-sectional shape of the light emitted from the illumination optical system 1 of the exposure apparatus. In addition, these patterns have sizes which reflect the value of the coherence factor σ expressing the size of illumination.

In addition, images which reflect the intensities of the diffraction lights 6, 7a, and 7b are formed on the wafer 5. The positive and negative first-order diffraction lights 7a and 7b are partially shielded by the aperture stop at the pupil plane 4a of the projection optical system 4 and their shapes are chipped thereby.

This kind of photoresist pattern is observed, for example, by an optical microscope, and a boundary between an area where photoresist was stripped and an area where photoresist was remained is defined. Specifically, the boundaries between the diffraction patterns 32, 33a, 33b, and the other areas are the boundaries defined here.

Figure 5:
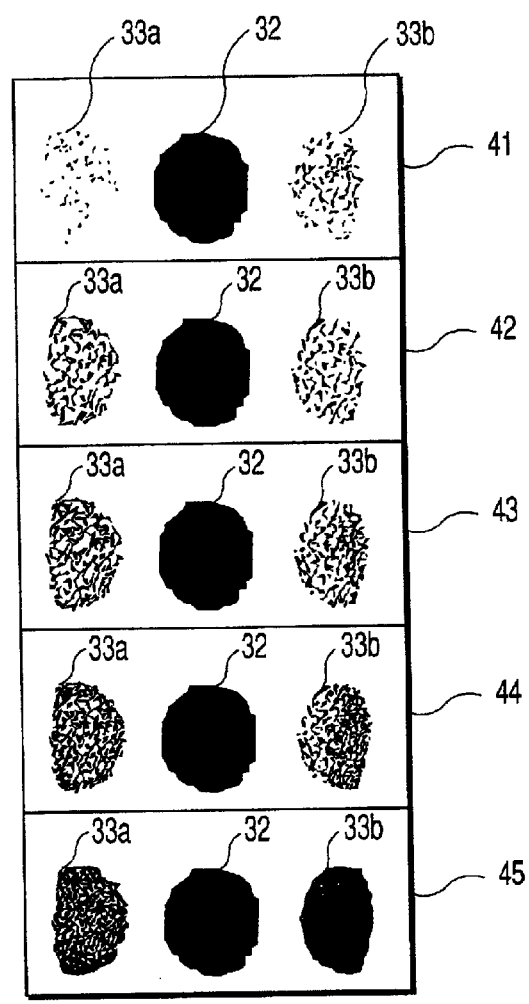
FIG. 5 are plan views showing photoresist patterns obtained by five times of pattern exposure according to five kinds of exposure doses according to the embodiment.
Figure 6A:
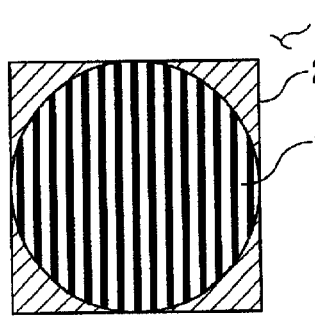
FIGS. 6A, 6B, 6C, 6D, 6E, 6F, 6G, 6H are views showing a modification example of the embodiment in which inspections are made in a method of changing the duty ratio.
Figure 6E:
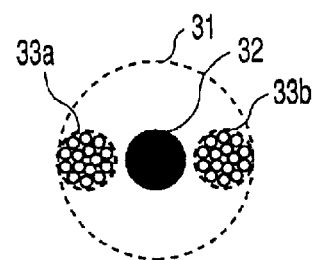
Figure 6B:
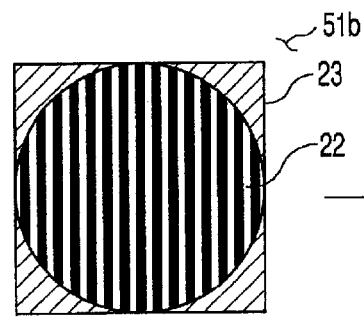
Figure 6F:
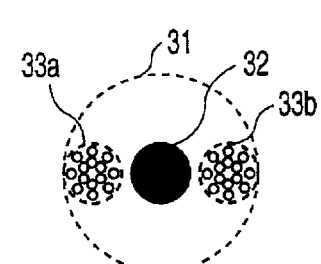
Figure 6C:
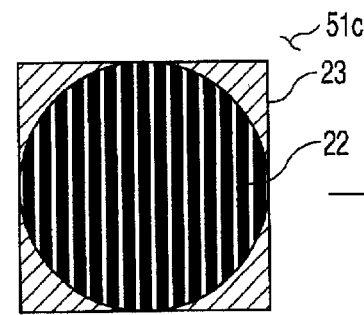
Figure 6G:
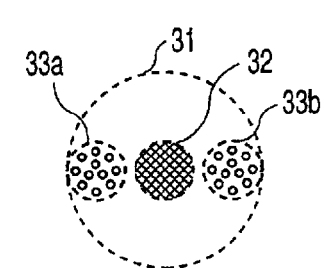
Figure 6D:
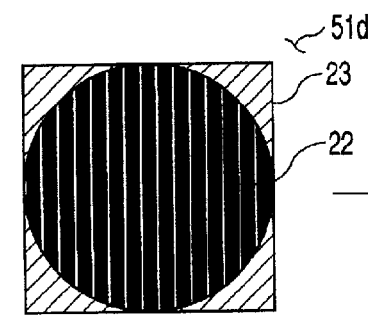
Figure 6H:
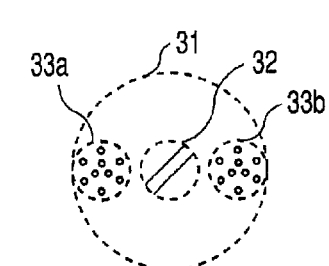
Figures 7A, 7E:
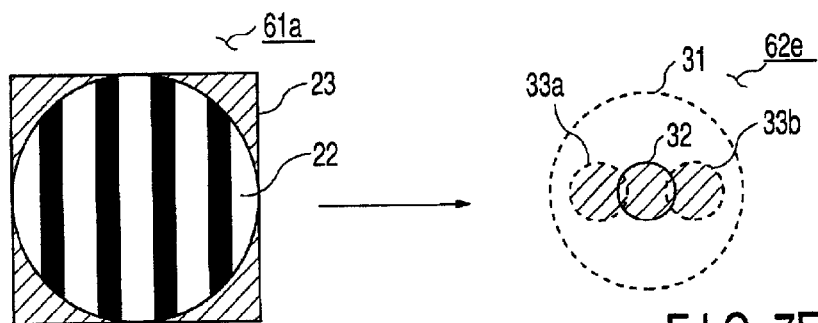
FIGS. 7A, 7B, 7C, 7D, 7E, 7F, 7G, 7H are views showing a modification example of the embodiment in which diffraction patterns having a plurality of periods are used to make an inspection.
Figures 7B, 7F:
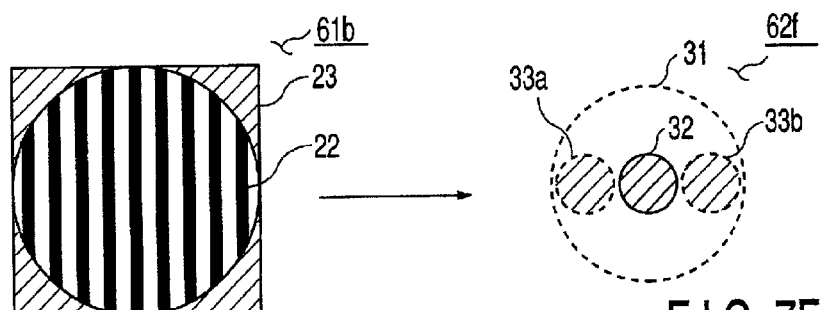
Figures 7C, 7G:
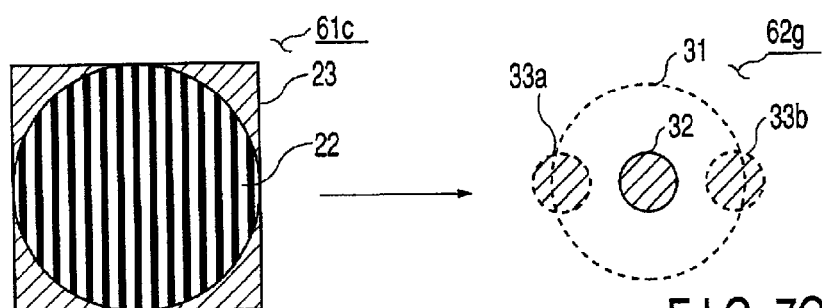
Figures 7D, 7H:
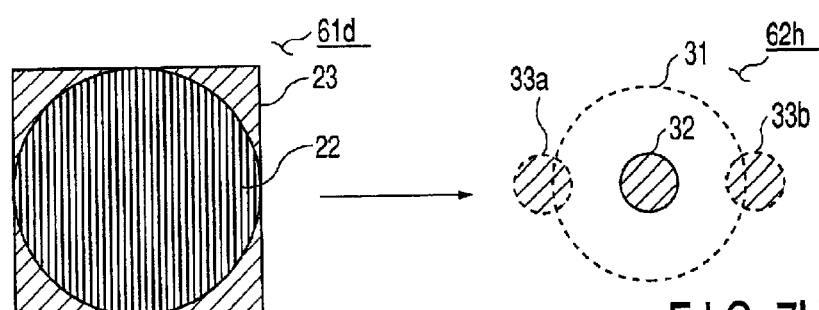

Pattern exposure explained above is carried out for a plurality of times with the exposure dose changed. In the present embodiment, for example, exposure is carried out five times. FIG. 5 shows plan views of photoresist patterns obtained through five times of exposure. References 41 to 45 respectively show plan views of photoresist patterns at exposure doses. The photoresist pattern 41 shows the case where the exposure dose is the lowest from which the exposure dose increases in the order of 42, 43, . . . . The photoresist pattern 45 shows the case where the exposure dose is the highest.

As shown in FIG. 5, it is known that the sizes of the diffraction light patterns 32, 33a, and 33b vary by changing the exposure dose. Primary diffraction light patterns 33a and 33b which cannot substantially appeared at a low exposure amount can appear more clearly as the exposure dose is increased. If the exposure dose thus varies, the boundaries between the diffraction patterns 32, 33a, and 33b vary accordingly.

Based of the five kinds of photoresist patterns 41 to 45 obtained by thus changing the exposure dose, a difference is obtained between the positive and negative first-order diffraction lights. Specifically, a shape of a diffraction light pattern as a reference (which will be hereinafter called a reference pattern) is determined. Further, patterns are selected each of which is most similar to this reference pattern from the five kinds of photoresist patterns, thereby to measure the exposure dose of the selected pattern. For example, the exposure dose when the positive first-order diffraction light pattern 33a becomes a reference is expressed as Ma, and the exposure dose when the negative diffraction light pattern 33b becomes a reference is expressed as Mb.

Further, the light intensity is calculated from the obtained exposure doses Ma and Mb based on the inverse proportional relationship between the light intensities and the exposure doses. Therefore, $1/Ma:1/Mb=Ia:Ib$ is obtained where Ia is a light intensity at which the positive first-order diffraction light pattern 33a is finished to have a reference shape, and Ib is a light intensity at which the negative first-order diffraction light pattern 33b is finished to have a reference shape. For example, if $Ma:1/Mb=9:10$ is given, the ratio of the diffraction light intensities is $Ia:Ib=1/9:1/10=10:9$.

In case of an ideal projection optical system, positive and negative diffraction lights which has passed through the projection optical system have an equal intensity, and therefore, the diffraction light intensities Ia and Ib become equal to each other. Meanwhile, if the film thickness of an anti-reflection film attached to the surface of a lens forming part of the projection optical system is not partially a desirable value because of the non-uniformity of the film thickness of the anti-reflection film or the lens itself has light absorption characteristics, the light transmittance is lowered at that part. The positive first-order diffraction lights are similar to negative first-order diffraction lights right after occurrence, and the positive and negative first-order diffraction lights have passed through the inside of the projection optical system, so each of the positive and negative first-order diffraction lights can be passed through the different paths with each own transmittance. As a result, the intensity differs between the positive and negative first-order diffraction lights. In the above example, it is apparent that the difference of the transmittance therebetween is 10:9 where expressed as a ratio. This ratio indicates a transmittance ratio of the light paths through which the positive and negative first-order diffraction lights has passed. As described above, it is possible to inspect the transmittance of the projection optical system, based on the exposure doses Ma and Mb.

Thus, according to the present embodiment, the periphery of the diffraction pattern where light transmission parts and opaque parts are repeated at a finite period is shielded by a opaque area, and the pattern is arranged with the pattern forming surface reversed from the state of actual pattern exposure, so that light from the illumination optical system is let pass through the photomask. In this manner, a change of the light transmittance depending on the path of the projection optical system can be measured in a state in which the photomask and the wafer are not conjugate with respect to the projection optical system.

The present invention is not limited to the embodiment described above. Although a pattern having a light transmission part and a opaque part, the pattern width of which is at a ratio of 1:1, is used as the line and space pattern, the present invention is not limited thereto but the ratio may be set to any ratio that can generate positive and negative first-order diffraction lights.

Although an inspection has been made with the exposure dose changed, the ratio of the light intensity may be measured by another method. For example, a plurality of patterns having one same period and one same shape may be provided, and pattern exposure may be carried out while changing the duty ratio of each pattern, i.e., the ratio of the length of the light transmission parts to the period of the patterns. In this case, the projection optical system can be inspected through one exposure by respectively forming patterns having different duty ratios on photomasks.

FIGS. 6A to 6H are explanatory views for principles in which exposure of one time is enough by adopting the method of changing the duty ratio. References 51a to 51d in FIGS. 6A to 6D denote mask patterns formed on one photomask. FIGS. 6E to 6H show schematically photoresist patterns obtained respectively from the mask patterns 51a to 51d.

Although the mask patterns 51a to 51d have a common point that a hole point pattern 22 with a diameter of 80 μm (as dimensions on a photomask) is formed in each opaque area 23, they have different duty ratios from each other. The duty ratio decreases in the order from the pattern 51a. Therefore, the pattern 51a has the highest duty ratio and the pattern 51d has the lowest duty ratio.

If a pattern is transferred with use of the patterns 51a to 51d having four kinds of duty ratios and one same period, the shapes of the respective photoresist patterns become different from each other, as shown in FIGS. 6E to 6H. More specifically, the diffraction light patterns 32, 33a, and 33b become different from each other. Although the diffraction light patterns 32, 33a, and 33b are expressed as circular shapes in FIG. 4, the patterns have thus circular shapes in case where the light irradiated from the illumination optical system has a circular irradiation area. An illumination optical system can be constructed by an aggregation of a plurality of point light sources, as specifically shown in FIGS. 6E to 6H.

Accordingly, the diffraction light patterns 32, 33a, and 33b are constructed by an aggregation of a plurality of circular patterns. By changing the duty ratio, the light intensity of the first-order diffraction light which has occurred can be changed. In case of the line-and-space pattern, the relationship between the duty ratio and the light intensity of the first-order diffraction light is expressed by the following expression:

$$I = I0 \sin^2(\pi x)$$

where x is the duty ratio, I is the light intensity of the first-order diffraction light, and I0 is a proportionality constant. Therefore, the same information as that obtained in case of exposing one same pattern with a plurality of different exposure doses can be obtained by performing exposures with use of these patterns 51a to 51d. Although this modification shows a case where patterns having different duty ratios are arranged on one photomask, the patterns may naturally be provided on a plurality of photomasks.

In addition, the period of the diffraction pattern 24 is set to 1.6 μm in the present embodiment. However, the invention is not limited thereto. A more detailed inspection can be achieved by a plurality of diffraction patterns not having one same diffraction pattern having one single period as in the present invention but having a plurality of periods. A modification example in which an inspection is carried out with use of diffraction patterns having a plurality of periods will be explained with reference to FIGS. 7A to 7H.

The references 61a to 61d shown in FIGS. 7A to 7D denote mask patterns formed on one photomask. FIGS. 7E to 7H schematically show photoresist patterns on a wafer, which are respectively obtained by mask patterns 61a to 61d.

The mask patterns 61a to 61d have a common point that a hole pattern 22 having a diameter of 80 μm is formed in each opaque area 23. These patterns, however, have periods different from each other. The period decreases in the order from the pattern 61a. Therefore, the pattern 61a has the largest period and the pattern 61d has the smallest period. The diffraction patterns of the patterns 61a to 61d have a common duty ratio of 0.5.

If a pattern is transferred with use of the patterns 61a to 61d having pattern periods of these four kinds and one same duty ratio, transfer positions of positive and negative first-order diffraction light patterns 33a and 33b as shown in FIGS. 7E to 7H differ. This is based on the principle that the light paths of the positive and negative first-order diffraction lights 7a and 7b can be changed by changing the period of the diffraction grating as described previously. Accordingly, the light paths of the positive and negative first-order diffraction lights 7a and 7b differ in the projection optical system 4. Measurement of the positive and negative first-order diffraction lights 7a and 7b that have passed these different paths indicates measurement of light that has passed through the vicinity of the center of a pupil plane forming part of the projection optical system 4 up to light that has passed through the vicinity of the periphery of the pupil plane.

These differences between the light paths apply in the same manner to the photoresist patterns. The component which runs straight after passing the photomask 3 is irradiated on the vicinity of the center of the light reach area 31, and the component which runs at a large diffraction angle after passing the photomask 3 is irradiated on the peripheral part of the light reach area 31. Accordingly, as shown in FIGS. 6E to 6H, observation of light diffraction patterns 33a and 33b formed at a plurality of positions means that information of intensities of lights in the radial direction of the projection optical system. Thus, the light transmittance distribution of the light path with respect to the radial direction of the projection optical system can be measured by thus using a plurality of periodic patterns.

The periods of the diffraction patterns may be provided so as to cover all the diameters in the radial directions of the circular area indicated by the light reach area 31. In this manner, the distribution of the light transmittance of the lens forming part of the projection optical system can be inspected with respect to all positions on one diameter. In addition, patterns having these plural periods may be provided on one photomask. In this manner, a large amount of information can be obtained by one time of exposure, and the inspection time is shortened. As a result, measurement becomes simple and easy.

Although the present embodiment shows patterns in which the lengthwise directions of lines are arranged in the upward and downward direction, the present invention is not limited thereto. By using patterns in which lengthwise directions of lines are arranged in a plurality of directions, the light transmittance distribution of the light path with respect to the angular direction of the projection optical system can be measured.

Figure 8A:
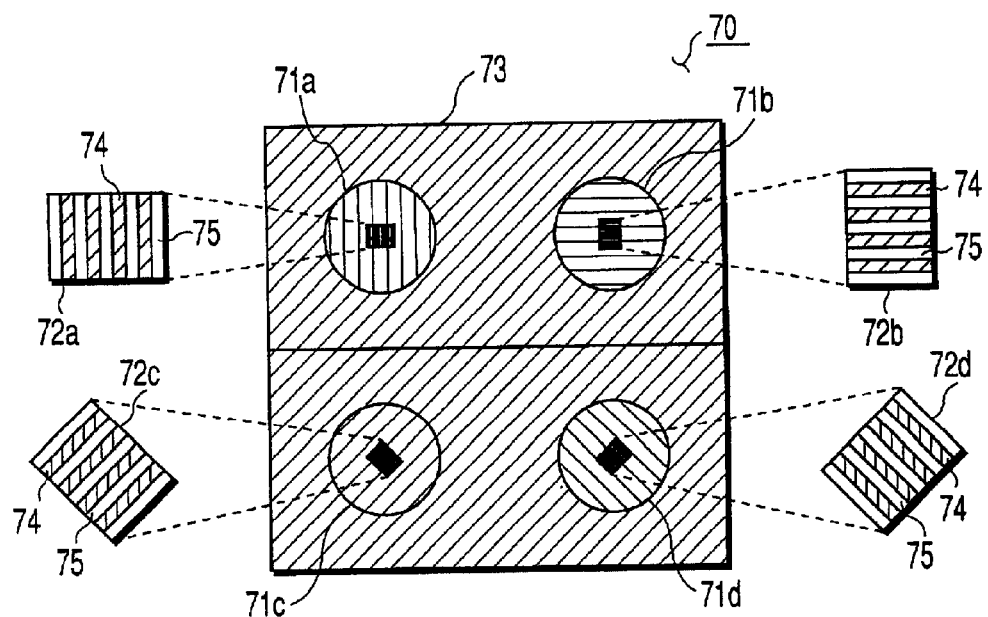
FIGS. 8A to 8B are views showing a modification example of the embodiment in which inspections are carried out with use of diffraction patterns which have line lengthwise directions in a plurality of directions.
Figure 8B:
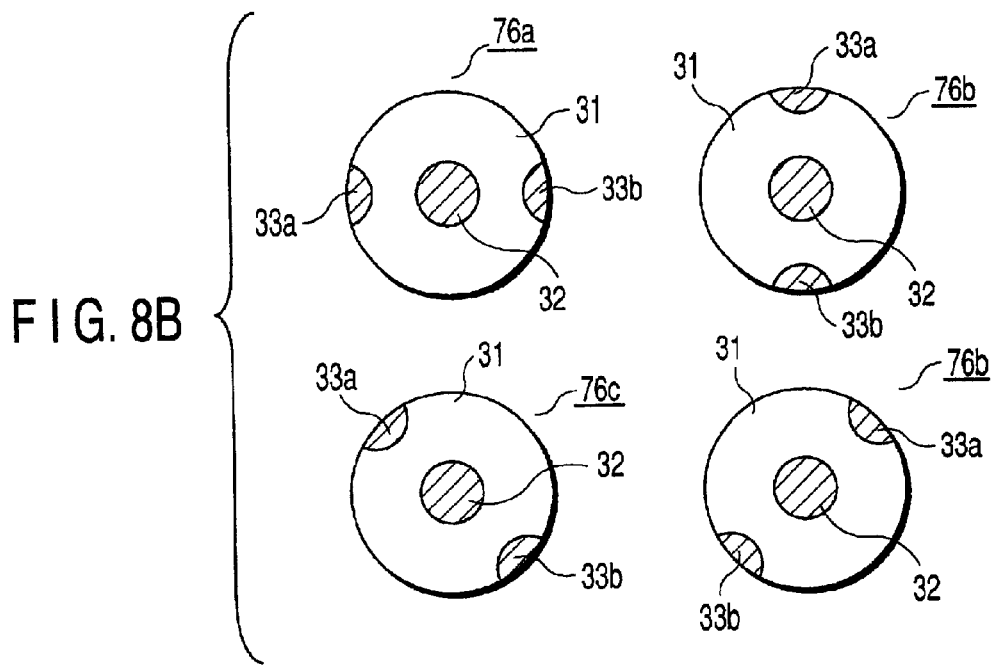

FIGS. 8A and 8B are views showing principles on which an inspection is carried out with use of a pattern in which the lengthwise directions of lines are oriented in a plurality of directions. As shown in FIG. 8A, pinhole patterns 71a to 71d having one same diameter of 80 μm are formed on one photomask 70. A diffraction pattern is formed in each of these pinhole patterns 71a to 71d. Note that the other area than the patterns 71a to 71d is a opaque area 73. FIG. 8A shows enlarged views of the diffraction patterns 72a to 72d in the patterns 71a to 71d. As can be seen from the enlarged views of the diffraction patterns 72a to 72d, the diffraction patterns 72a to 72d are line and space patterns each constructed by opaque parts 74 and light transmission parts 75, and have one same duty ratio at an equal period. The diffraction patterns 72a to 72d are different from each other in lengthwise directions of their lengthwise directions of the line and space patterns.

FIG. 8B schematically shows photoresist patterns formed by the photomask 70 shown in FIG. 8A. The patterns to be transferred by the patterns 71a to 71d respectively correspond to the patterns 76a to 76d. As can be seen from FIG. 8B, a zeroth-order diffraction light pattern 32 and positive and negative first-order diffraction light patterns 33a and 33b are formed in the light reach area 31. The positive and negative first-order diffraction light patterns 33a and 33b are formed at positions shifted in the direction vertical to the lengthwise direction of lines of the diffraction patterns. Accordingly, it is understood that the positions of the formed patterns vary by changing the lengthwise direction of lines of the diffraction patterns.

By thus using a photomask where diffraction gratings are formed in a plurality of directions, it is possible to measure the transmittance of the projection optical system corresponding to the plurality of directions from the center.

The example shown in FIGS. 8A and 8B has been explained with reference to patterns whose lengthwise directions are oriented in four directions. Needless to say, however, the present invention is not limited thereto. For example, the distribution of the light transmittance of the lens forming part of the projection optical system can be inspected with respect to all the directions viewed from the center if lengthwise directions of the lines of the diffraction patterns are oriented in the directions so as to cover all the peripheral part of the light reach area 31 by the first-order diffraction light. For example, in case a photomask where eight kinds of diffraction patterns are formed in eight direction at respective angles (22.5°×N) (N: 0, 1, 2, . . . , 7) with respect to a reference straight line, measurement point is as two times as in the case of FIGS. 8A and 8B, thereby more precise measurement can be performed than in the case of FIGS. 8A and 8B. In addition, it is unnecessary to arrange these plural periodic patterns on one photomask, like in the case of the modification shown in FIGS. 6A to 6H.

(Second Embodiment)

FIGS. 9A to 11 are explanatory views for explaining an inspection method for an exposure apparatus according to the second embodiment of the present invention. The present embodiment will be explained also with reference to an example of the case where an inspection is carried out with respect to a KrF excimer reduction projection apparatus (λ: 248 nm, NA: 0.6, σ: 0.3, and magnification M of the mask: 4), like the first embodiment. Detailed explanation of the structure of the exposure apparatus will therefore be omitted. Characteristic points of the present embodiment exist in the shape of the diffraction grating in the pinhole which is drawn on the photomask used for inspection. Although line and space patterns are arranged in the pinhole patterns in the first embodiment, square grating patterns are arranged in the present embodiment.

FIG. 9A is a view showing the entire structure of the photomask 80 used in the present embodiment. Note that the present embodiment can be applied to the exposure apparatus shown in FIG. 2 by providing the photomask 80 in place of the photomask 3 used in the first embodiment. As shown in FIG. 9A, in the photomask 80 having a size of 15 cm×15 cm, pinhole patterns 81 are arranged at an equal interval. The diameter of each pinhole pattern 81 is 80 μm like in the first embodiment, and the pinhole patterns 81 are arranged such that the distance from each pinhole pattern 81 to another nearest pinhole pattern 81 is 1200 μm.

The diameter of each pinhole pattern 81 is set to 80 μm and the distance between pinhole patterns 81 is set to 1200 μm from the following reasons.

Each pinhole pattern 81 in the present embodiment is based on the same principles as those basing a pinhole camera. It is well known that the resolution of a pinhole camera is optimized when $r=(1\lambda)^{1/2}$ is satisfied where the radius of the pinhole is r, the light path length from the pinhole to the surface where an image is projected is 1, and the wavelength of light is λ.

In case of the present embodiment, pattern images to be transferred to a wafer 7 need only to be at non-conjugate positions with respect to the projection optical system, i.e., the resolution needs to be high in the surface side of the mask. Accordingly, an image with high resolution can be obtained by obtaining a product of the thickness d of the photomask 3 and a refractive index n of glass forming part of the body of the photomask 3. In the present embodiment, however, the resolution needs not always be the highest but needs only to satisfy the following expression (1).

$$0.4(nd\lambda)^{1/2} \le r \le (nd\lambda)^{1/2} \qquad (1)$$

If a pattern having an area equal to a circle having a radius r, i.e., $\pi r^2$ is considered other than a circular pattern, it is only necessary to satisfy the following expression (2).

$$0.4(nd\lambda)^{1/2} \le r \le 10(nd\lambda)^{1/2} \qquad (2)$$

In the case of the present embodiment, n=1.5, d=6.35 mm, and λ=248 nm are satisfied, so it is understood that the diameter of the pinhole pattern 81 satisfies the above expression (1).

Figure 10:
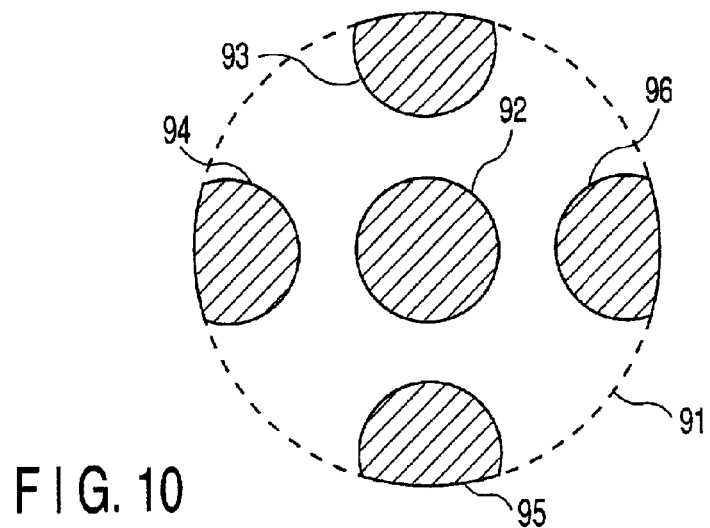
FIG. 10 is a view schematically showing photoresist pattern obtained by pattern exposure according to the embodiment.

If exposure is carried out under the above-described condition, the diameter of the diffraction light reach area 91 in FIG. 10 is about 300 μm. That is, the positions where individual patterns are transferred must be distant from each other at least by 300 nm long on the wafer in order that images of individual pinholes do not overlap each other. In the present embodiment, the magnification M of the mask=4 is given so that the interval distance between pinhole patterns on the photomask must be 1200 μm or more. The pinhole pattern layout on the photomask 80 satisfies this condition.

FIG. 9B is an enlarged view showing the vicinity of a pinhole pattern 81 arranged on the photomask 80. FIG. 9C is a more enlarged view showing a part of the pattern illustrated in FIG. 9B. As shown in FIGS. 9B and 9C, the pinhole pattern 81 is comprised of a opaque part 82 and light transmission parts 83.

The opaque part 82 extends linearly in the longitudinal and lateral directions of the figure such that the light transmission parts 83 disposed in a matrix are arranged to be apart from each other, constructing a grating-like shape. In this manner, the light transmission parts function as a diffraction grating with respect to two directions of X- and Y-directions. Where k is a line width of the opaque part 82 and a is the length of the side of each light transmission part 83, k=0.8 μm and a=0.8 μm are given and the pattern period is 1.6 μm.

Thus, a plurality of pinholes patterns 81 shown in FIGS. 9B and 9C are provided, and it is therefore possible to observe changes of the transmittance within the exposure area in the projection optical system.

With use of the photomask 80 described above, pattern exposure is carried out in a non-conjugate state in which the wafer 5 and the photomask 80 are not conjugate with respect to the projection optical system. Like the first embodiment, exposure is carried out for a plurality of times with different exposure doses.

FIG. 10 is a view schematically showing photoresist pattern obtained by the exposure described above. As shown in FIG. 10, the inside of the light reach area 91 is an area where the light that passes through the projection optical system 4 can reach the wafer 5. The diffraction patterns provided on the photomask 80 constitute a grating pattern which is periodical in two directions. The grating pattern therefore generates first-order diffraction light not only in one direction but also in a direction vertical to the one direction. Accordingly, one zeroth-order diffraction pattern 92 and four first-order diffraction light patterns 93 to 96 are generated on the wafer 5. These diffraction light patterns 92 to 96 are similar to a cross-sectional shape of light emitted from the illumination optical system 1 of the exposure apparatus. In addition, images that reflect respective diffraction lights are formed on the wafer 5. The first-order diffraction lights 93 to 96 are partially shielded by the aperture stop in the periphery of the pupil 4a of the projection optical system 4 to have a shape chipped thereby.

This kind of photoresist pattern is observed, for example, by an optical microscope, and boundaries are defined between areas where photoresist was stripped and areas where photoresist was remained. Specifically, boundaries between the diffraction light patterns 92 to 96 and the other area are the boundaries defined in this case.

Figure 11:
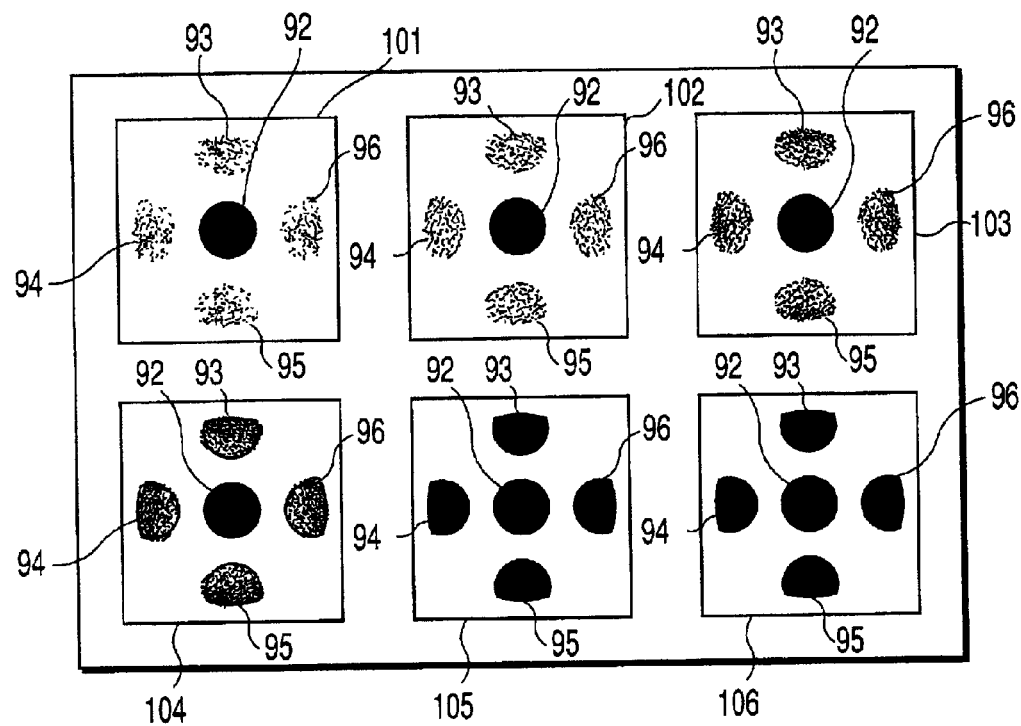
FIG. 11 is a plan view showing photoresist patterns obtained by six times of exposure depending on six kinds of exposure doses, according the embodiment.

Pattern exposure described above is carried out for a plurality of times while changing the exposure dose, and as a result, photoresist patterns having different forming areas can be obtained. FIG. 11 is a plan view showing photoresist patterns obtained by total six times of exposure. As shown in FIG. 11, a photoresist pattern 101 corresponds to a case where minimum exposure dose can be given, a photoresist pattern 102 can be obtained by an exposure with larger exposure dose than in the case of the photoresist pattern 101, a photoresist pattern 103 can be obtained by an exposure with larger exposure dose than in the case of the photoresist pattern 102, . . . , and a photoresist pattern 106 can be obtained by an exposure with largest exposure dose. The sizes of the first-order diffraction light patterns 93 to 96 vary by changing the exposure dose. It can be understood that the first-order diffraction light patterns 93 to 96 that can not substantially observed at a low exposure dose can be observed clearly by increasing the exposure dose. Thus, the boundaries of the diffraction light patterns 93 to 96 vary as the exposure dose varies.

Based on the six kinds of photoresist patterns 101 to 106 obtained by changing the exposure dose, the intensity ratio of each of the first-order diffraction lights 93 to 96 is obtained. Note that the process for obtaining the intensity ratio is the same as that of the first embodiment and detailed explanation thereof will be omitted.

Thus, according to the present embodiment, an inspection is carried out with use of a photomask on which a grating-like diffraction pattern is provided. In this manner, the same advantages as those of the first embodiment can be achieved, and information concerning the projection optical system can be obtained with respect to one direction and another direction vertical to the one direction.

(Third Embodiment)

FIGS. 12A, 12B and 13 are explanatory views for an inspection method for an exposure apparatus according to the third embodiment of the present invention. The present embodiment will be explained with reference to a case of making an inspection of a KrF excimer laser reduction projection exposure apparatus (λ: 248 nm, NA: 0.6, σ: 0.3, magnification M of the mask: 4) like the first embodiment. Therefore, detailed explanation of the structure of the exposure apparatus will be omitted herefrom. The present embodiment is characterized in the shape of the diffraction grating in each pinhole drawn on the photomask used for the inspection. In the first and second embodiments, line and space patterns or square grating-like patterns are arranged in each pinhole pattern. In the present embodiment, however, a honeycomb-like pattern is arranged.

FIG. 12A is a view showing a main part of the photomask used in the present embodiment. As shown in FIG. 12A, pinhole patterns 112 each having a diameter of 80 μm are arranged, surrounded by a opaque area 111. Although the present embodiment does not show the entire structure of the photomask, either a case where only one single pinhole pattern 112 are formed or a plurality of pinhole patterns are formed can be applied to the present embodiment.

FIG. 12B is an enlarged view showing the inside of a pinhole pattern 112 shown in FIG. 12A. The pinhole pattern 112 is constructed by a opaque part 113 and circular light transmission parts 114.

A large number of light transmission parts 114 are formed in the hole pattern 111 and are arranged such that the light transmission parts 114 have periodic relationships in three directions between each other. That is, the light transmission parts 114 are arranged at an equal interval in one direction 115, at an equal interval in a direction at 60° to the direction 115, and at an equal interval in a direction at 120° to the direction 115. A light passes through the light transmission parts 114 arranged adjacent to each other at equal intervals in the directions 115 to 117, and a diffraction occurs due to lights which have passed through the light transmission parts 114 arranged adjacent to each other.

Note that regular hexagonal boundaries separating the light transmission parts 114 each other are drawn merely to facilitate the description, so all of the other area including these boundaries than the light transmission parts 114 is the opaque part 113.

Using a photomask where pinhole patterns 112 shown above are arranged, an inspection is carried out like the first and second embodiments. Specifically, exposure is carried out for a plurality of times at different exposure doses. FIG. 13 shows an example of photoresist patterns formed on the wafer 5 in this manner. As shown in FIG. 13, the inside of the light reach area 121 is an area where the light that has passed through the photomask and the projection optical system 4 from the illumination optical system 1 can reach the wafer. A honeycomb-like pattern provided on the photomask according to the present embodiment has periods in three directions, and therefore, diffraction phenomena occur in six directions. Accordingly, one zeroth-order diffraction light pattern 122 and six first-order diffraction light patterns 123 to 128 are generated.

The photoresist patterns of this kind are observed, for example, by an optical microscope. It is possible to obtain a changes of the transmittance of the projection optical system depending on the path of light of the projection optical system by obtaining a ratio of the light intensity with use of the same manner as that of the first or second embodiment, based on the result of this observation, like the first or second embodiment.

Thus, according to the present embodiment, the same advantages as those of the first and second embodiments are obtained and an inspection is carried out with use of patterns having periods in three directions, so first-order diffraction light patterns can be obtained in six positions. Accordingly, the light transmittance distribution of the light path with respect to the angular direction of the projection optical system can be measured in a shorter time than in the first and second embodiments.

(Fourth Embodiment)

Figure 16:
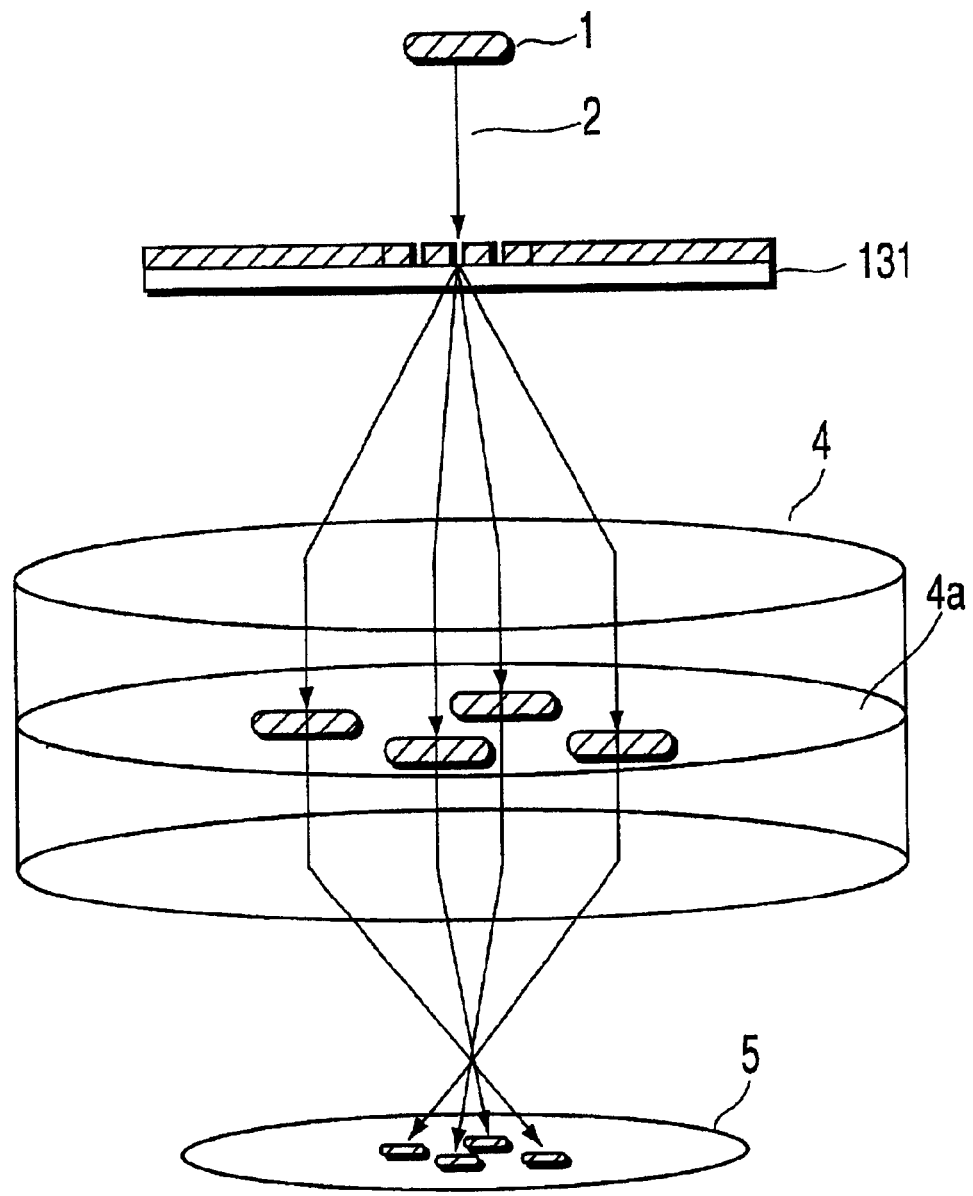
FIG. 16 is a schematic view showing light paths of first-order diffraction light in an inspection according to the embodiment.

FIGS. 14 to 16 are explanatory views for an inspection method for an exposure apparatus, according to the fourth embodiment of the present invention. In the present embodiment, explanation will be made with reference to a case of an example in which a KrF excimer laser reduction projection exposure apparatus (λ: 248 nm, NA: 0.6, σ: 0.3, mask magnification M: 4) is inspected. Therefore, detailed explanation of the structure of the exposure apparatus will be omitted herefrom. The present embodiment is characterized in that a phase shift mask is used to make an inspection.

FIG. 14 is a view showing the entire structure of a photomask 131 used in the present embodiment. Note that the present embodiment can be applied to the exposure apparatus shown in FIG. 2 by providing the photomask 131 in place of the photomask 3 used in the first embodiment. AS shown in FIG. 14, a pinhole pattern 132 having a diameter of 80 μm is provided on the photomask 131, and the other area than the pinhole pattern 132 is a opaque part 133. Note that only one opaque part 133 is illustrated in FIG. 14 for simplicity, a plurality of opaque parts 133 can be arranged like in FIG. 9A, so that each opaque part 133 is formed at least to the position range of 1200 μm from the pinhole pattern 132.

The inside of the pinhole pattern 132 is comprised of a attenuated phase shift part 134 and a light transmission part 135. The light transmission part 135 is comprised of a plurality of square patterns which are arranged like a grating. The ratio between the pattern width of the attenuated phase shift part 134 and the pattern width of the light transmission part 135 is 11:9, namely the duty ratio of the diffraction grating is 045, and the pattern period is 3.2 μm. The light transmittance of the attenuated phase shift part 134 is 24.5% and a phase difference between a light which pass through the light transmission part 135 and a light which pass through the attenuated phase shift part 134 is 180°.

With use of the photomask 131 described above, pattern exposure is carried out in a non-conjugate state in which the wafer 5 and the photomask 131 are not conjugate with respect to the projection optical system, like the first embodiment. Specifically, exposure is carried out with pattern-forming surface attached to the mask stage of the exposure apparatus and reversed from that in the case of actual device pattern exposure. In addition, like the first embodiment, exposure is carried out for a plurality of times at different exposure doses.

FIG. 15A is a view schematically showing photoresist patterns obtained by the exposure described above. The inside of the light reach area 141 is an area where the light that passes through the photomask 131 and the projection optical system 4 from the illumination optical system 1 can reach the wafer 5. The diffraction patterns provided on the photomask 131 constitute a grating pattern which is periodical in two directions. The grating pattern therefore generates first-order diffraction light not only in one direction but also in another direction vertical to the one direction. Accordingly, four first-order diffraction light patterns 142 to 145 are created on the wafer 5. These diffraction light patterns 142 to 145 are similar to a cross-sectional shape of light emitted from the illumination optical system 1 of the exposure apparatus.

The light intensity ratio between zeroth-order diffraction light and the first-order diffraction light which is generated with the diffraction grating pattern illustrated in the FIG. 13 is expressed by the following expression:

$$s0:s1 = [-y + x^2(1+y)]^2 : [x(1+y)\sin(\pi x)/\pi]^2$$

Where s0 is the light intensity of the zeroth-order diffraction light, s1 is the light intensity of the first-order diffraction light, x is a duty ratio, and y is an amplitude transmittance. In the case of the attenuated phase shift mask used in the present embodiment, x is 0.45 and y is 0.245. Thus, the light intensity of the zeroth-order diffraction light is less than 1/500 of the light intensity of the first-order diffraction light. Therefore, the intensity of generated zeroth-order first-order diffraction light is very weak so that the pattern due to zeroth-order diffraction light is not transferred to the wafer.

This kind of photoresist pattern is observed, for example, by an optical microscope, and boundaries are defined where photoresist was stripped and areas where photoresist was remained. Specifically, boundaries between the diffraction light patterns 142 to 145 and the other area are the boundaries defined in this case.

Pattern exposure described above is carried out for a plurality of times while changing the exposure dose, and as a result, photoresist patterns having different forming areas can be obtained. Light intensity ratios between first-order diffraction light 142 to 145 can be obtained based on these photoresist patterns. Note that the process for obtaining the intensity ratio is the same as that of the first embodiment, and therefore detailed explanation thereof will be omitted herefrom.

Advantages obtained by making an inspection with use of a attenuated phase shift mask as described above will be explained with reference to FIG. 16. FIG. 16 is a view schematically showing the paths of the first-order diffraction light in the present embodiment. In case where the photomask has the structure as described above, the intensity of the zeroth-order diffraction light which runs straight is too weak to expose the photoresist on the wafer 5. Note that zeroth-order light is omitted from FIG. 16. Primary diffraction lights are generated in four directions at predetermined angles, and reach the wafer 5 through paths different from each other, respectively, thereby exposing the photoresist.

In the present embodiment, no zeroth-order light is generated, and it is therefore possible to measure components of the first-order diffraction light that are difficult to obtain dye to existence of zeroth-order diffraction light in the first to third embodiment. For comparison, FIG. 15B schematically shows photoresist patterns in case of using a normal mask not formed of a attenuated phase shift mask but formed of only a light transmission part and opaque parts. As shown in FIG. 15B, areas where the first-order diffraction light patterns 142 to 145 are formed overlap an area where the zeroth-order diffraction pattern 146 is formed on the wafer 5. These overlapping areas are areas that are formed by light which passes through a part close to the center axis of the optical system. Thus, in the parts where the zeroth-order diffraction light and the first-order diffraction light overlap each other, it is impossible to observe only the first-order diffraction light patterns 142 to 145. Accordingly, it is not possible to obtain information concerning the light transmittance of the projection optical system 4. In contrast, if a attenuated phase shift mask is used as in the present embodiment, the zeroth-order diffraction light becomes a very weak component so that no zeroth-order diffraction light 146 is formed. Accordingly, an overlapping area as shown in FIG. 15B is not generated but the light transmittance of the path through which the first-order diffraction light which reaches an area close to the center of the projection optical system 4 can be measured.

Of course, the shape of each pinhole pattern 132, the shape of the diffraction pattern in each pinhole pattern 132, the directions thereof, and the σ value thereof and the like are not limited to values described above. Any photomask can be used as long as it is a attenuated phase shift mask and generates diffraction light. In addition, the phase difference between the attenuated phase shift part 134 and the opaque part 135 needs not always be 180° but may be 120° or so. In this case, it is desirable to adjust the phase difference and the same measurement as well as the above measurement can be done.

The present invention is not limited to the embodiments described above. The embodiments described above show only the case where measurement is carried out with use of first-order diffraction light, but can be carried out with use of second-order diffraction light or higher. In addition, zeroth-order diffraction light can be used for measurement. In this case, light intensities of zeroth-order diffraction light and first-order diffraction light are previously calculated, and zeroth-order diffraction light and first-order diffraction light actually obtained by transferring patterns may be compared with each other, based on the light intensities.

Figure 17A:
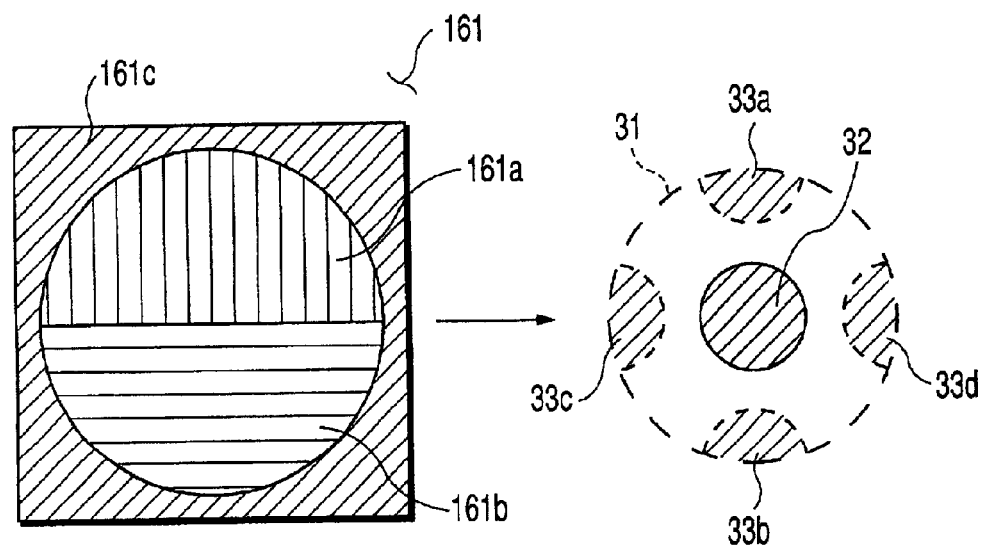
FIGS. 17A and 17B are plan views showing modification examples of pinhole patterns formed on photomasks of the present invention.
Figure 17B:
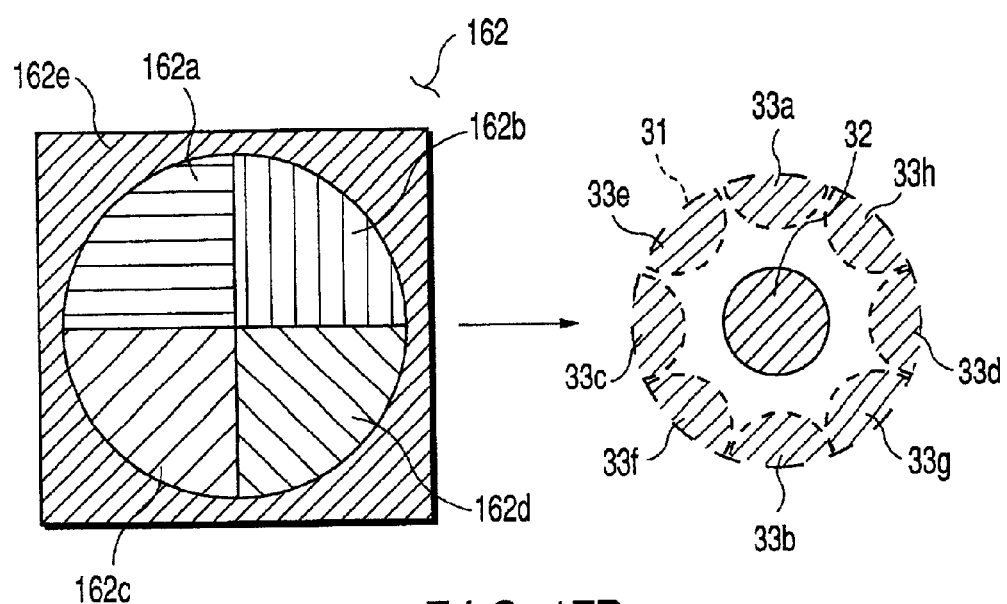

In the modification shown in FIGS. 8A and 8B according to the first embodiment, diffraction patterns having different line lengthwise directions are arranged individually as four pinhole patterns 71a to 71d. However, it is possible to arrange a diffraction pattern in which one pinhole pattern includes a plurality of line lengthwise directions. FIGS. 17A and 17B are views showing this modification example. In the mask pattern 161 shown in FIG. 17A, diffraction patterns 161a and 161b having two kinds of line lengthwise directions are arranged in a opaque area 161c. In the mask pattern 162 shown in FIG. 17B, diffraction patterns 162a to 162d having four kinds of line lengthwise directions are arranged in a opaque area 162e. In case of photoresist patterns transferred by the mask pattern 161 shown in FIG. 17A, a zeroth-order diffraction light pattern 32 and four first-order diffraction light patterns 33a to 33d are formed. In case of the photoresist patterns transferred by the mask pattern 132 shown in FIG. 17B, a zeroth-order diffraction light pattern 32 and eight first-order diffraction light patterns 33a to 33h are formed.

By thus making an inspection with a diffraction pattern having a plurality of line lengthwise directions in one pinhole pattern, the same advantages as those of the modification example shown in FIGS. 8A and 8B can be obtained and more remarkable advantages can further be obtained than them. That is, in the case of the modification example shown in FIGS. 8A and 8B, information concerning eight directions from the center of a projection optical system is obtained by synthesizing four obtained photoresist patterns, with respect to a projection optical system. In the case of the example shown in FIGS. 17A and 17B, information concerning a plurality of directions can be obtained from one photoresist pattern without synthesizing photoresist patterns. Accordingly, inspections can be made without being influenced from errors between respective images when synthesizing images obtained from photoresist patterns. It is therefore possible to make an inspection with high precision.

Alternatively, an alternating phase shift mask may be used. For example, in the diffraction patterns shown in FIG. 3B in the embodiment described above, lights which pass through light transmission parts 26 adjacent to each other may be arranged to have a phase difference of 180° between each other. In this case, the duty ratio may be any value. Although the explanation has been made with reference to FIG. 3B, the phase difference between lights which pass through the closest light transmission parts needs only to be set to 180°. For example, in case of FIG. 9B, it is only necessary that light which passes through each of light transmission parts 83 positioned to a light transmission part 83 as a reference in the longitudinal and lateral directions from have a phase difference of 180° with respect to light which passes through the light transmission part 83 as the reference.

Figure 18A:
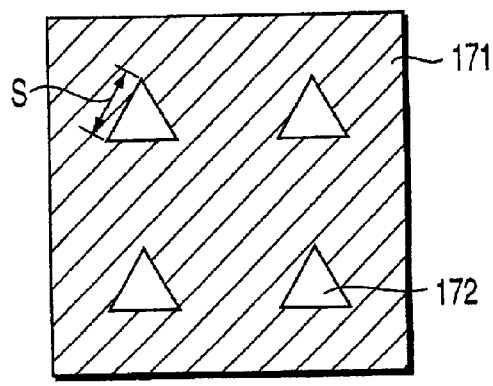
FIGS. 18A, 18B, 18C are plan views showing modification examples of photomasks of the present invention.
Figure 18B:
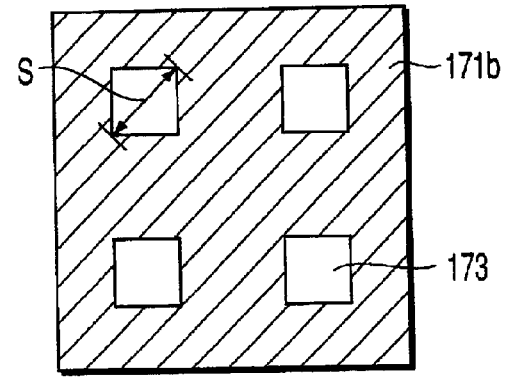
Figure 18C:
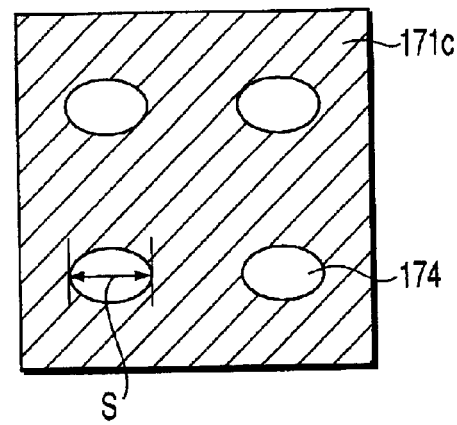

Although circular pinhole patterns are obtained as patterns arranged on a photomask, the present invention is not limited thereto. FIGS. 18A to 18C show modification examples of the photomask. Any pinhole patterns can be used as long as the periphery of each hole pattern is shielded for a predetermined distance by a opaque part, like a pattern in which triangular hole patterns 172 are formed in the photomask 171a, as shown in FIG. 18A, a pattern in which rectangular hole patterns 173 are formed in a photomask 171b, as shown in FIG. 18B, and a pattern in which elliptic hole patterns 174 are formed in a photomask 171c, as shown in FIG. 18C. If the hole patterns have a shape whose size is equal to a circular hole pattern, the same diffraction light as that in the embodiments described above is generated and the same photoresist pattern as that in the embodiment is obtained.

In case of thus using triangular, rectangular, or elliptic hole patterns, the condition indicated by the expression (1) in the first embodiment is normalized as in the following expression (3).

$$0.4(nd\lambda)^{1/2} \leq s/2 \leq (nd\lambda)^{1/2} \tag{3}$$

The s in this expression is a length of the longest line among lengths of lines connecting arbitrary two points on the boundaries between the light transmission patterns and the opaque pattern.

Although the above embodiments shows the cases where a line and space pattern, a square grating pattern, and a honeycomb-like pattern are used as diffraction gratings arranged inside the pinhole patterns, the present invention is not limited thereto. Any diffraction patterns can be used as long as the patterns generate dispersive diffraction light, for example, like a checkered grating pattern, a pillar pattern in which opaque parts and light transmission parts of these patterns are reversed, and the like.

Figure 19:
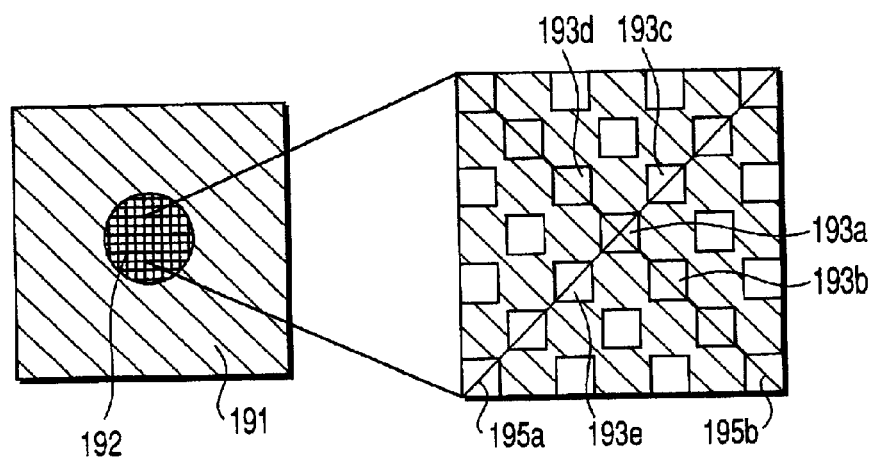
FIG. 19 is a plan view showing modification examples of photomasks of the present invention.

FIG. 19 shows an example of a checkered grating pattern. As shown in FIG. 19, a pinhole pattern 192 is provided, surrounded by a opaque area 191. The point that a plurality of pinhole patterns of this kind are provided in an actual mask pattern is the same as FIGS. 8A, 9A, 12A, and the like.

Figure 20:
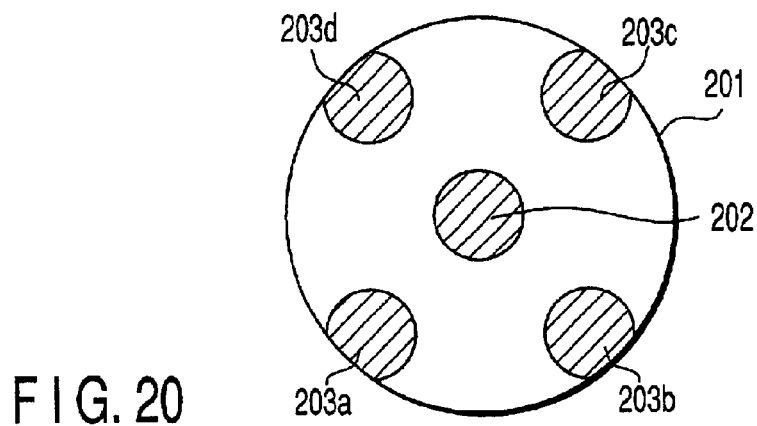
FIG. 20 is a view schematically showing photoresist patterns obtained by the pattern in the FIG. 19.

As can be seen from an enlarged view of this pinhole pattern in FIG. 19, this pinhole pattern is constructed by a opaque part 194 and light transmission parts 193. Each light transmission part 193 is surrounded by the opaque part 193 and is a square. Suppose that one of the square light transmission parts 193 is used as a reference and is denoted by 193a. Light-transmissible parts 193b, 193c, 193d, and 193e having their gravity centers on diagonals 195a and 195b are provided at positions closest to the light transmission part 193a. If each light transmission part is used as a reference, light transmission parts are provided at closest positions under the same condition as those of the light transmission part 193a. FIG. 20 shows an example of a resist pattern which is transferred to a wafer by the checkered-grating pinhole pattern constructed as described above. As shown in FIG. 20, a zeroth-order diffraction light pattern 202 is formed by zeroth-order diffraction light, and first-order diffraction light patterns 203a to 203d are formed by first-order diffraction lights, within a right reach area 201. By thus using a checkered grating pattern, first-order diffraction light patterns can be formed in four directions. Further, first-order diffraction light patterns can be formed in the diagonal directions since closest light transmission parts are adjacent to each other in the diagonal directions (45° and 135° with respect to the longitudinal and lateral directions of each light transmission part 193). This is a significant advantage, considering that a mask manufactured by a drawing device using an electron beam or light is normally created by drawing rectangular pixels as units. That is, it is necessary to manufacture a mask pattern in which longitudinal and lateral directions of a rectangle are inclined obliquely, in order to form first-order diffraction light patterns in the oblique directions without using a checkered grating pattern as described above. However, manufacture of a mask pattern of this kind is relatively difficult due to drawing techniques.

Figure 22:
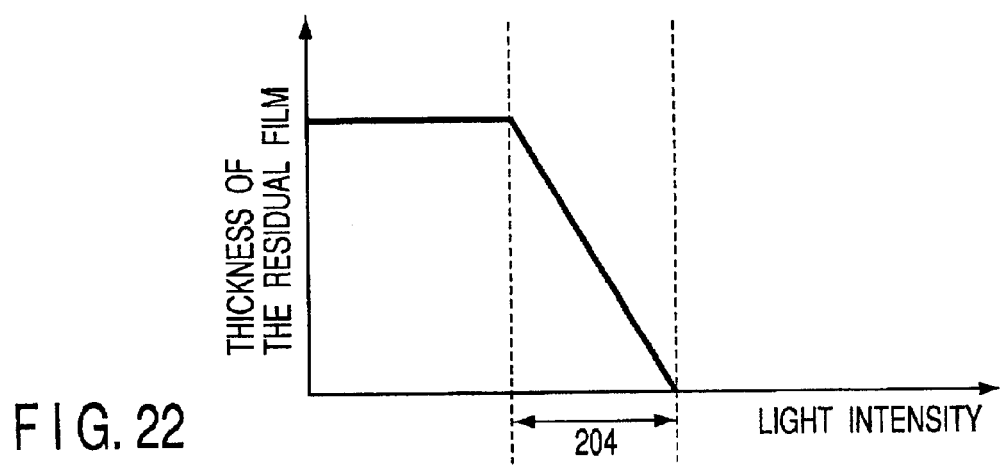
FIG. 22 is a graph showing a sensitivity curve.

Further, in the embodiments described above, a plurality of transfer patterns obtained by changing the exposure dose are subjected to image processing, and images are synthesized, thereby to obtain a contour plot of intensities. However, the present invention is not limited thereto. For example, a light intensity distribution may be obtained from the film thickness of photoresist pattern obtained by inspection exposure, and intensity distributions of respective patterns thus obtained may be synthesized, thereby to obtain a contour plot of light intensity distributions. Based on the contour plot of light intensity distributions, the light transmittance of the projection optical system can be obtained. In the case of this method, the light transmittance can be obtained by preparing and referring to a sensitivity curve expressing the relationship between the film thickness of the photoresist which has exposed and the light intensity, without using a resist having no proportional relationship. It is preferable to use photoresist in which the light intensity and the film thickness of photoresist patterns constitute a proportional relationship or a similar relationship. Of course, a light transmittance can be obtained by the exposure with appropriate exposure doses and referring to a sensitivity curve expressing the relationship between the film thickness and the light intensity, without using a resist having no proportional relationship. For example, if a sensitivity curve is expressed such as in FIG. 22, it is preferable to be exposed with exposure doses with respect to a range 204 of the intensity in which the slope of the sensitivity curve is relatively larger than another range.

This measurement method will now be explained with a resist pattern shown in FIG. 4 taken as an example.

With a resist pattern of this kind, a film thickness distribution is measured, for example, by a film thickness measuring device. Changes of the film thickness are obtained throughout the entire area where diffraction patterns of positive and negative first-order diffraction lights are transferred. Specifically, the changes can be expressed in form of a contour map.

Figure 21:
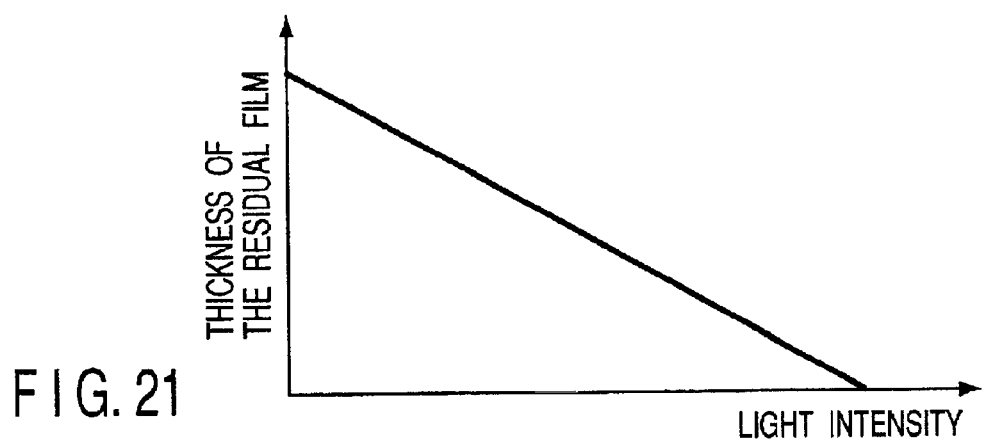
FIG. 21 is a graph showing a sensitivity curve.

In general, the sensitivity and decomposition characteristics of photoresist with respect to light differ depending on the kinds of photoresist. For example, a sensitivity curve as shown in FIG. 21, which shows the relationship between the light intensity and the thickness of a residual film, is obtained. Further, the contour map of the film thickness distribution as described above is substituted into a distribution graph of intensity of light irradiated on a wafer, by referring to the sensitivity curve. From a light intensity distribution graph thus obtained, a difference between positive and negative first-order diffraction lights is obtained.

Although explanation has been made with use of FIG. 4 in this example, the same is also applicable to other resist patterns.

Although a KrF excimer laser light source is used as an inspection target of the exposure apparatus, the same advantages as those of the present invention can be obtained even in case where, for example, an i-ray or ArF excimer laser, $F_2$ excimer laser, or the like is used as a light source. In addition, the mask magnification M and NA are not limited to values shown in the above embodiments. Although the photomask 3 is explained as a mask for inspection of an exposure apparatus, an actual pattern that is used for actual pattern exposure may be arranged with its surfaces reversed from those of a pinhole pattern used for inspection. In this manner, it is possible to carry out actual pattern exposure and to observe simply the light transmittance of the projection optical system on real time, using a pattern for inspection for every time of the actual exposure. In this case, the pinhole pattern and the actual pattern should preferably be arranged apart from each other to an extent that both patterns do not interfere with each other.

As has been explained above, according to the present invention, it is possible to specify changes of the light transmittance of the projection optical system depending on the paths of lights.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for inspecting an exposure apparatus, comprising:

a step of guiding light emitted from an illumination optical system to a photomask where a pattern is formed of an optical member including a light transmission pattern as a diffraction grating pattern, in which a light transmission part and an opaque part are repeated in a predetermined direction, a plurality of ratios are given between a length of the light transmission part and a length of the opaque part in a repetition direction, and a periphery of the light transmission pattern is shielded by an opaque area, such that a plurality of ratios are given between the light transmission part and the opaque part;

a step of irradiating diffraction light, which has passed through the photomask, on a projection optical system, thereby to transfer a pattern reflecting an intensity distribution of the diffraction light to a wafer; and a step of measuring a change of transmittance depending on a light path of the projection optical system, based on a pattern image of the diffraction light transferred to the wafer.

2. A method according to claim 1, wherein said pattern transfer is performed in which the photomask and the wafer are non-conjugate with respect to the projection optical system.

3. A method according to claim 1, wherein, where NA is a numerical aperture of the projection optical system in a side of the wafer, λ is a exposure length, σ is a coherence factor, and M is a magnification of the photomask, the diffraction grating pattern has a period which satisfies $$p > M\lambda/NA(1+\sigma).$$

4. A method according to claim 1, wherein the non-conjugate state in which the photomask and the wafer are non-conjugate with respect to the projection optical system is realized by arranging the opaque part of the light optical member on a surface opposite to a surface where the optical member of the photomask used for device pattern exposure is arranged.

5. A method according to claim 1, wherein, where a length of a longest line among lengths of lines connecting arbitrary two points positioned on a boundary to the opaque part, of the opaque part of the light transmission pattern, is 2r, a thickness of the photomask is d, an exposure wavelength is λ, and a refractive index of a material of the photomask at the exposure wavelength λ is n, a relationship of $0.4(nd\lambda)^{1/2} \leq r \leq (nd\lambda)^{1/2}$ is satisfied.

6. A method according to claim 5, wherein the light transmission pattern is a circular pattern having a radius r.

7. A method according to claim 6, wherein where, of the light pattern, an area surrounded by the opaque area is expressed $\lambda r^2$, a thickness of the photomask is d, an exposure wavelength is λ, and a material of the photomask has a refractive index of n, a relationship of $0.4(nd\lambda)^{1/2} \leq r \leq 10 (nd\lambda)^{1/2}$ is satisfied.

8. A method according to claim 1, wherein
the pattern formed on the wafer is made of a predetermined material, and
the change of the transmittance is measured by measuring a film thickness of the pattern transferred to the wafer and by obtaining a light intensity of the diffraction light, based on a predetermined relationship between a film thickness of the predetermined material and an irradiation light intensity.

9. A method according to claim 1, wherein the predetermined relationship between the film thickness of the predetermined material and the light intensity is a sensitivity curve expressing the relationship between the film thickness of the predetermined material and the light intensity.

10. A method according to claim 1, wherein a change of the transmittance is measured in a manner that a boundary between an area where photoresist was stripped and an area where photoresist was remained is regarded as a equal-intensity contour curve, a plurality of equal-intensity contour curves each being the equal-intensity contour curve are obtained respectively under different conditions, and the plurality of equal-intensity contour curves obtained are layered thereby to obtain an equal-intensity contour plot.

11. A method for inspecting an exposure device, comprising:
a step of guiding light emitted from an illumination optical system to a photomask where a pattern is formed of an optical member including a light transmission pattern as a diffraction grating pattern, in which a light transmission part and an opaque part are repeated in a predetermined direction, a plurality of ratios are given between a length of the light transmission part and a length of the opaque part in a repetition direction, phases of lights which pass through adjacent light transmission parts with the opaque part inserted therebetween differs from each other substantially by 180°, and a periphery of the light transmission pattern is shielded by an opaque area, such that a plurality of ratios are given between the light transmission part and the opaque part;
a step of irradiating diffraction light, which has passed through the photomask, onto a projection optical system, thereby to transfer the pattern to a wafer and to form a pattern reflecting an intensity distribution of the diffraction light; and
a step of measuring a change of transmittance depending on a light path of the projection optical system, based on a pattern image of the diffraction light transferred to the wafer.

12. A method according to claim 11, wherein said pattern transfer is performed in which the photomask and the wafer are non-conjugate with respect to the projection optical system.

13. A method according to claim 11, wherein
the pattern formed on the wafer is made of a predetermined material, and
the change of the transmittance is measured by measuring a film thickness of the pattern transferred to the wafer and by obtaining a light intensity of the diffraction light, based on a predetermined relationship between a film thickness of the predetermined material and an irradiation light intensity.

14. A method according to claim 11, wherein the predetermined relationship between the film thickness of the predetermined material and the light intensity is a sensitivity curve expressing the relationship between the film thickness of the predetermined material and the light intensity.

15. A method according to claim 11, wherein a change of the transmittance is measured in a manner that a boundary between an area where photoresist was stripped and an area where photoresist was remained is regarded as a equal-intensity contour curve, a plurality of equal-intensity contour curves each being the equal-intensity contour curve are obtained respectively under different conditions, and the plurality of equal-intensity contour curves obtained are layered thereby to obtain an equal-intensity contour plot.

* * * * *